United States Patent
Ervin

(10) Patent No.: US 9,235,689 B2
(45) Date of Patent: Jan. 12, 2016

(54) METHOD, SYSTEM AND APPARATUS FOR CONTROLLING PATIENT ACCESS TO MEDICAMENTS

(71) Applicant: MEDICASAFE, INC., New York, NY (US)

(72) Inventor: Matthew J. Ervin, New York, NY (US)

(73) Assignee: MEDICASAFE, INC., New York, NY (US)

( * ) Notice: Subject to any disclaimer, the term of this patent is extended or adjusted under 35 U.S.C. 154(b) by 107 days.

(21) Appl. No.: 13/836,944

(22) Filed: Mar. 15, 2013

(65) Prior Publication Data

US 2013/0226339 A1 Aug. 29, 2013

Related U.S. Application Data

(63) Continuation-in-part of application No. 12/895,611, filed on Sep. 30, 2010, now Pat. No. 8,666,539, which is a continuation-in-part of application No. 11/892,612, filed on Aug. 24, 2007, now Pat. No. 7,996,106.

(60) Provisional application No. 60/906,525, filed on Mar. 13, 2007.

(51) Int. Cl.
| | |
|---|---|
| *G06F 17/00* | (2006.01) |
| *G06F 19/00* | (2011.01) |
| *A61J 1/03* | (2006.01) |
| *G07F 17/00* | (2006.01) |
| *A61J 7/04* | (2006.01) |

(52) U.S. Cl.
CPC ............... *G06F 19/3462* (2013.01); *A61J 1/03* (2013.01); *G07F 17/0092* (2013.01); *A61J 7/0409* (2013.01); *A61J 7/0436* (2015.05)

(58) Field of Classification Search
CPC ....... G07F 17/0092; A61J 7/0084; A61J 7/04; G06F 19/3462; A61B 5/00
See application file for complete search history.

(56) References Cited

U.S. PATENT DOCUMENTS

| | | | |
|---|---|---|---|
| 5,036,462 A | 7/1991 | Kaufman et al. | |
| 5,084,828 A * | 1/1992 | Kaufman et al. | ............. 700/242 |

(Continued)

FOREIGN PATENT DOCUMENTS

| | | |
|---|---|---|
| EP | 1316929 | 6/2003 |
| WO | WO-0209001 | 1/2002 |

(Continued)

OTHER PUBLICATIONS

Partial Supplementary European Search Report from EP 11833091.9, mailed on Jun. 10, 2015.

*Primary Examiner* — Timothy Waggoner
(74) *Attorney, Agent, or Firm* — Stroock & Stroock & Lavan LLP

(57) ABSTRACT

Systems and methods for detecting a likely misuse of a medicament by a user. The system includes a computer communicatively coupled with a dispensing device. The computer receives a usage pattern of a medicament by the user as indicated by the dispensing device and a result of a test correlating with an actual consumption of the medicament by the user. Based on the usage pattern, the computer computes an estimated result of a test corresponding to the at least one predetermined test. Based on a comparison between the estimated result and the test result, a determination is made as to whether the user has likely misused the medicament.

15 Claims, 14 Drawing Sheets

(56) References Cited

U.S. PATENT DOCUMENTS

| | | | |
|---|---|---|---|
| 5,562,232 A | 10/1996 | Pearson | |
| 5,642,731 A * | 7/1997 | Kehr | 600/300 |
| 6,124,136 A * | 9/2000 | Kell | 436/111 |
| 6,330,491 B1 | 12/2001 | Lion | |
| 6,438,451 B1 | 8/2002 | Lion | |
| 6,471,087 B1 * | 10/2002 | Shusterman | 221/2 |
| 6,570,488 B2 | 5/2003 | Kucharczyk et al. | |
| 6,892,941 B2 | 5/2005 | Rosenblum | |
| 6,973,371 B1 | 12/2005 | Benouali | |
| 7,178,688 B2 | 2/2007 | Naufel et al. | |
| 7,366,675 B1 | 4/2008 | Walker et al. | |
| 7,585,680 B2 * | 9/2009 | Larson et al. | 436/169 |
| 7,743,923 B2 | 6/2010 | Conley | |
| 8,636,172 B2 * | 1/2014 | Dunn | 221/261 |
| 8,751,039 B1 * | 6/2014 | Macoviak et al. | 700/244 |
| 8,874,260 B2 * | 10/2014 | Saltsov | 700/244 |
| 2001/0028308 A1 | 10/2001 | De La Huerga | |
| 2004/0158349 A1 | 8/2004 | Bonney et al. | |
| 2006/0071011 A1 | 4/2006 | Varvarelis et al. | |
| 2006/0155607 A1 | 7/2006 | Bahir | |
| 2006/0218015 A1 | 9/2006 | Walker et al. | |
| 2008/0035661 A1 | 2/2008 | Handfield et al. | |
| 2008/0114490 A1 | 5/2008 | Jean-Pierre | |
| 2008/0228317 A1 | 9/2008 | Ervin | |
| 2009/0015245 A1 | 1/2009 | Burrows | |

FOREIGN PATENT DOCUMENTS

| | | |
|---|---|---|
| WO | WO-02078594 | 10/2002 |
| WO | WO-2006070359 | 7/2006 |
| WO | WO-2006106405 | 10/2006 |
| WO | 2009/080309 A1 | 7/2009 |
| WO | 2010/008377 A1 | 1/2010 |

* cited by examiner

FIGURE 12
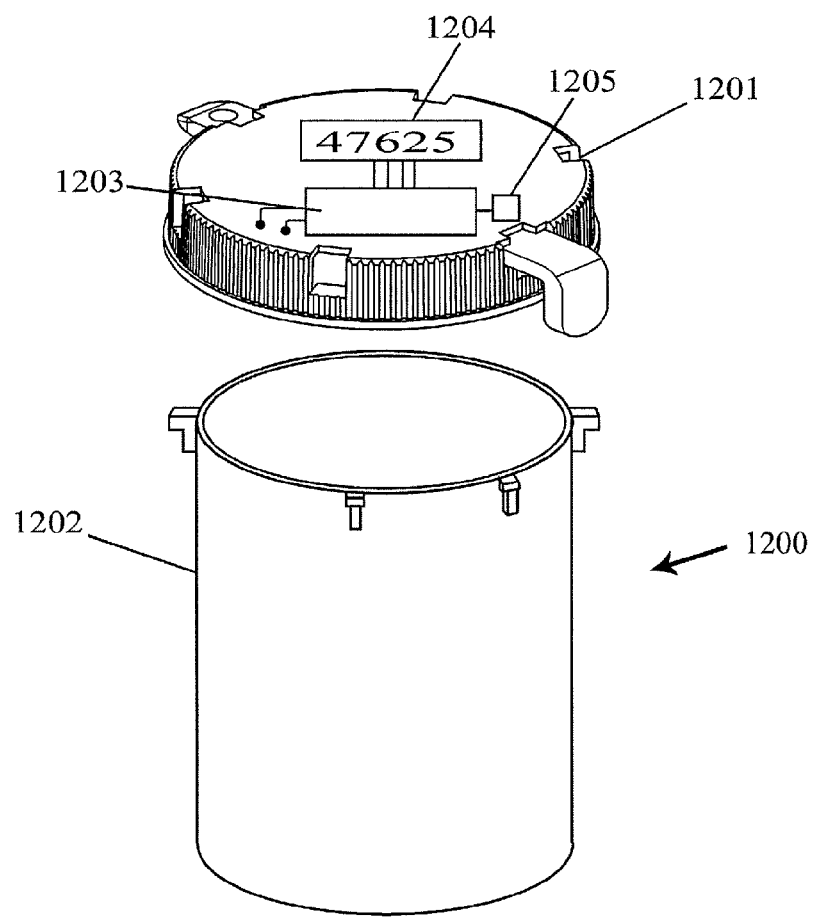
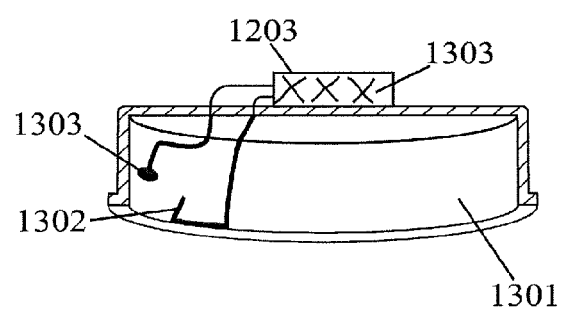
FIGURE 13

METHOD, SYSTEM AND APPARATUS FOR CONTROLLING PATIENT ACCESS TO MEDICAMENTS

CROSS REFERENCE TO RELATED APPLICATIONS

This application is a continuation-in-part application of U.S. patent application Ser. No. 12/895,611, which claims the benefit of U.S. patent application Ser. No. 11/892,612 filed on Aug. 24, 2007, now U.S. Pat. No. 7,996,106, and U.S. Provisional Application No. 60/906,525 filed on Mar. 13, 2007, the contents of which are incorporated by reference herein in their entirety.

BACKGROUND

Various medications are prescribed to combat illnesses and ailments. The use of prescribed medication, usually provided in pill form, has increased as medical science has progressed. Likewise, advancements in medical science have increased the selection, application and potency of prescription medications. Moreover, various diseases, conditions and illnesses that once required or allowed a patient to opt for hospitalization are now commonly treated on an out-patient basis through a prescribed medication regimen.

For the above reasons and more, many medications including many drugs in pill form are now regularly self-administered under little to no supervision. Self-administration of medication increases the possibility that a patient will fail to comply with directions regarding such things as dosage and timing. Non-compliance can greatly diminish the effectiveness of the treatment as well as increase the likelihood of harm to the patient, neither of which are desirable. Further, non-compliance can increase healthcare costs and consume healthcare resources that could be allocated elsewhere but for the non-compliance.

Even when unsupervised by medical professionals, patients must follow their treatment regimens when travelling or at home, just as students must do their homework outside of school. However, even motivated pupils will lose engagement and show poor compliance with their homework regimen when there is a failure to review or correct the pupils' homework. Similarly, outside the medical setting, patients are largely unmonitored and research confirms that they lose interest in their treatment regimens. This "lack of engagement" can be mitigated by the invention described herein which is designed to facilitate patient monitoring and patient feedback assessment. Of particular benefit, the invention creates a "Hawthorne effect"—inducing the patient to follow treatment more carefully.

It is estimated that less than 50% of written prescriptions are taken as prescribed. This non-compliance results in the non-desirable effects of greatly diminishing the effectiveness of the treatment and increasing the likelihood of harm to the patient. Furthermore, the patient's non-compliance can result in increases in healthcare costs and in the consumption of healthcare resources that could be allocated elsewhere but for the non-compliance. A co-related problem is that during doctor visits, the patient may not be able to accurately relay medical information because the patient's previous behaviors, symptoms, and side-effects are vague memories.

Abuse such as recreational use or unauthorized distribution is always a societal concern. Often abuse is interrelated to dependency. The risk of dependency is of particular concern when the prescribed medication is known to be habit-forming or outright addictive. Although the risk of dependency is particularly acute when the patient is known to be high-risk (i.e. susceptible to abuse and addiction), dependency remains a risk with all patients.

Thus, the risks associated with non-compliance are a real concern for doctors, pharmacists and manufacturers, among others. As a result, doctors often under-prescribe certain medications, thereby, lessening the benefits of the medication. Doctors and other healthcare professionals are also forced to make dependency risk determinations about their patients, which can put the patient and the doctor in an uncomfortable, possibly, compromising situation.

The patient's non-compliance with a prescribed medication regimen may result in underdosing, overdosing, medication abuse and dependency, all of which typically affect a patient's overall health and, in many cases, can be life-threatening.

Overdosing may result from the patient's unsound attempts to increase the therapeutic effectiveness of the medication, to cause self-inflicted harm, or to abuse or depend on medication. Overuse of certain medications, such as painkillers, has become a major societal concern. Healthcare professionals have no acceptable tools to detect abuse patterns, to deter misuse, to limit diversion, or to optimize patient education for at-risk patients. As a result, doctors often under-prescribe abusable medications, thereby lessening the benefits of the medication. On the other hand, underdosing may result if the patient seeks to lower their prescription costs or to limit the prescription's side effects.

Underdosing and overdosing often occur by simple mistake or neglect, particularly when the patient is required to self-administer a complex regimen of medications. In order for a medical professional to respond with corrective action or change the treatment regimen, it would be beneficial for the medical professional to be made aware of the patient's deviation from the prescribed usage.

In an embodiment, the invention described herein provides a solution to the dilemma described above. This enables the gathering of useful information from a remote party, for example a patient, at an affordable cost. Moreover, this enables that information to be gathered from a device in a manner that virtually assures its accuracy. And this also enables that the verifiable dissemination of information to the device even though the device user may be unreliable.

In an embodiment, the invention enables the automatic and regular assessment of patients to create a useful data trail of symptoms, side-effects, and activity levels. This enables the approximate monitoring of a patient's medication usage pattern which is indicative of whether a patient is overusing or underusing medication. This also enables the deterring of unauthorized access to medication. Also, this enables the gathering of useful subjective information about a patient at an affordable cost.

In an embodiment, this invention enables the data gathered, both objective and subjective, to be combined into actionable reports for use by healthcare professionals to make better treatment decisions. This enables a doctor to assess whether or not there is an apparent pattern of progress and to determine whether a therapy is not working because of a drug or because of the patient's non-compliance. This enables reports that can help the doctor in determining these issues or allow a care team to make an evidence-based decision on whether to proceed with a drug therapy, or whether to change the drug.

Moreover, in an embodiment, this invention enables intervention in an automatic or semi-automatic manner, allowing the automatic (a) curtailing medication access when overuse is noted, (b) instigating reminders when underuse is detected, and (c) communicating educational messages at relevant moments, based on the subjective and objective data being gathered from the patient.

The invention described herein was conceived for use in a healthcare setting. But it has applicability in other settings, such as the monitoring of weapons, devices with dangerous qualities, or the monitoring of devices controlled by users prone to undesirable behavior or error.

Non-compliance with prescriptions for certain abuse-prone medications, e.g. opioid pain killers, often includes overuse or alternatively the diversion of the prescribed drugs. Overuse can result from "doctor shopping", wherein an individual sees multiple doctors to obtain overlapping prescriptions for the drugs being abused, or the mixing of prescribed drugs with illicitly obtained drugs. Diversion relates to the behavior of selling or otherwise disposing of medicaments rather than using them. It can be challenging for medical professionals to reliably identify those patients that are abusing or diverting medications, especially opioids.

SUMMARY

According to at least one embodiment, a method of managing and monitoring access to medications in a medicament dispensing device can include receiving identifying data from a user and evaluating whether or not to grant access to the medicaments based on the identifying data received. Identifying data can include data about the dispensing device, the status of the dispensing device, the identity of the patient, the treatment regimen prescribed, or the current condition of the patient. If a decision is made to grant access, either by default or as a result of analyzing the identifying data provided, then limited-use access authorization data can be provided. Limited-use access authorization data enables the dispensing device to dispense the medicaments up to a certain limit of use. The limited-use access authorization data can be communicated to the user by a variety of means, including via the telephone.

In another exemplary embodiment, a system for managing and monitoring access to medicaments can include an interfacing system configured to interface with a communicative intermediary and a dispensing device for dispensing the medicaments. The dispensing device can be capable of providing limited access to the medicaments in response to valid access authorization data. The access authorization data can be independently computable by both the device and the interfacing system and can be of limited use. Thus, limited access to the medicaments can be granted via communication of the valid limited-use authorization data from the interfacing system to a user via a communicative intermediary. Moreover, the status and the dispensing history of the device can be ascertained from the user by requesting device status information via the communicative intermediary. This information is requested as part of identifying data, and valid identifying data can be required prior to communicating valid access authorization data to the user of the dispending device, thus establishing a process whereby a user of the dispensing device has a strong incentive to communicate identifying information accurately and in a timely manner.

In yet another exemplary embodiment, a method of managing and monitoring access to medicaments can include a means for inputting identifying data, a means for authorizing the inputted identifying data and a means for outputting access authorization data.

In another exemplary embodiment, the invention enables a treatment optimization system built around patient dialog. The master system collects patient-reported data on symptoms, side-effects, or activities via phone or web. The master system can also collect objective, reliable data about medication usage patterns and other measures of patient health. For example, the master system can collect data about the patient's blood pressure, glucose levels, or weight. After processing this information, the master system can initiate appropriate patient education modules and compile actionable reports for use by a healthcare team. The master system can provide medical professionals the data needed to optimize treatments and allow patients to receive personalized behavioral support on a regular basis.

According to an exemplary embodiment of the invention, the master system may receive identifying data from a patient. The master system may then evaluate whether or not to grant access to the drugs or medicaments based on the identifying data received. Medicaments from a single prescription can be divided into multiple containers, each container requiring access authorization data, for example an access code. To access a container, a patient may input the access authorization data received from the master system.

The rate of usage of the medicaments can be approximately derived from the times at which the patient seeks access. For example, if the patient's medicaments are provided in containers that each contain a one week supply, and if the patient seeks access to a new medicament container every day, then the master system would indicate that the patient is overusing the medicaments. The master system can then limit the patient's overuse by withholding access authorization data. Alternatively, a healthcare professional can conclude that the patient is underusing their medication if the patient seeks access authorization data less frequently than expected, According to yet another exemplary embodiment of the invention, the pill container can be closed by a cap that detects when the cap is removed from the bottle. The pill container can generate and display a status code that represents the usage pattern of the pill container. A patient can be asked to relay this status code to the master system. The master system then decodes the status code. Based on the status code, the master system derives data that can be used to further refine estimates of when the patient sought access to medicaments. The master system may communicate with the patient via a communication channel. For example, the master system may communicate with the patient via telephone, web, or via a mobile communication device. The patient may also communicate data to the master system. For example, the patient may communicate data related to the patient's identity, their symptoms, side-effects, activities, the pill container's identification ID number or a status code displayed on the pill container. In response, the master system may communicate data to the patient that grants or withholds the patient's access to additional medicaments. The master system may also contain a data repository of all of the data collected from the patient and derived from observing the patient's behavior. The master system may collect this data into reports that can be useful to a healthcare professional. When the master system detects a pattern of medication misuse, the master system can automatically send an automated message to a patient or to a healthcare professional.

According to further embodiments of the present invention, systems and methods are provided to enable identification of potential misuse of medicaments, such as diversion or overuse. No additional labor is required by the treating physician. As the treating physician can receive a report that clearly signals abuse or diversion, appropriate action can be taken or the patient can be dissuaded from such behaviors (i.e. "Hawthorne effect").

BRIEF DESCRIPTION OF THE FIGURES

Advantages of embodiments of the present invention will be apparent from the following detailed description of the exemplary embodiments thereof, which description should be considered in conjunction with the accompanying drawings in which:

FIG. 12 is an illustration of another embodiment of an alternative exemplary embodiment of a pill cap containing electronics for logging opening of a pill bottle;

FIG. 13 is an exploded illustration of the pill cap in FIG. 12; and

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Figure 1:
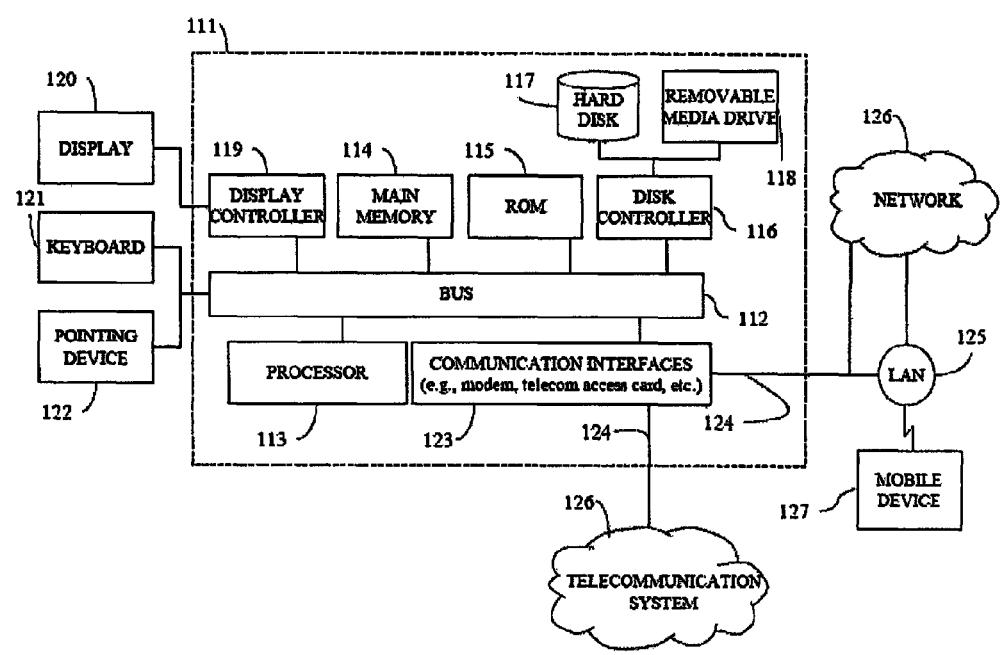
FIG. 1 is an exemplary diagram of a computer network.

FIG. 1 illustrates a computer system 111 upon which an embodiment of the present invention may be implemented. The computer system 111 includes a bus 112 or other communication mechanism for communicating information, and a processor 113 coupled with the bus 112 for processing the information. The computer system 111 also includes a main memory 114, such as a random access memory (RAM) or other dynamic storage device (e.g., dynamic RAM (DRAM), static RAM (SRAM), and synchronous DRAM (SDRAM)), coupled to the bus 112 for storing information and instructions to be executed by processor 113. In addition, the main memory 114 may be used for storing temporary variables or other intermediate information during the execution of instructions by the processor 113. The computer system 111 further includes a read only memory (ROM) 115 or other static storage device (e.g., programmable ROM (PROM), erasable PROM (EPROM), and electrically erasable PROM (EEPROM)) coupled to the bus 112 for storing static information and instructions for the processor 113.

The computer system 111 also includes a disk controller 116 coupled to the bus 112 to control one or more storage devices for storing information and instructions, such as a magnetic hard disk 117, and a removable media drive 118 (e.g., floppy disk drive, read-only compact disc drive, read/write compact disc drive, compact disc jukebox, tape drive, and removable magneto-optical drive). The storage devices may be added to the computer system 111 using an appropriate device interface (e.g., small computer system interface (SCSI), integrated device electronics (IDE), enhanced-IDE (E-IDE), direct memory access (DMA), or ultra-DMA).

Further, exemplary embodiments include or incorporate at least one database which may store software, descriptive data, system data, digital images and any other data item required by the other components necessary to effectuate any embodiment of the present system and method known to one having ordinary skill in the art. The databases may be provided, for example, as a database management system (DBMS), a relational database management system (e.g., DB2, Oracle, SQL Server, My SQL, ACCESS, etc.), an object-oriented database management system (ODBMS), a file system or another conventional database package as a few non-limiting examples. The databases can be accessed via a Structure Query Language (SQL) or other tools known to one having skill in the art.

The computer system 111 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 111 may also include a display controller 119 coupled to the bus 112 to control a display 120, such as a cathode ray tube (CRT), liquid crystal display (LCD) or any other type of display, for displaying information to a computer user. The computer system includes input devices, such as a keyboard 121 and a pointing device 122, for interacting with a computer user and providing information to the processor 113. Additionally, a touch screen could be employed in conjunction with display 120. The pointing device 122, for example, may be a mouse, a trackball, or a pointing stick for communicating direction information and command selections to the processor 113 and for controlling cursor movement on the display 120. In addition, a printer may provide printed listings of data stored and/or generated by the computer system 111.

The computer system 111 performs a portion or all of the processing steps of the invention in response to the processor 113 executing one or more sequences of one or more instructions contained in a memory, such as the main memory 114. Such instructions may be read into the main memory 114 from another computer readable medium, such as a hard disk 117 or a removable media drive 118. One or more processors in a multi-processing arrangement may also be employed to execute the sequences of instructions contained in main memory 114. In alternative embodiments, hard-wired circuitry may be used in place of or in combination with software instructions. Thus, embodiments are not limited to any specific combination of hardware circuitry and software.

As stated above, the computer system 111 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 111, for driving a device or devices for implementing the invention, and for enabling the computer system 111 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 113 for execution. A computer readable medium may take many forms, including but not limited to, non-volatile media, volatile media, and transmission media. Non-volatile media includes, for example, optical, magnetic disks, and magneto-optical disks, such as the hard disk 117 or the removable media drive 118. Volatile media includes dynamic memory, such as the main memory 114. Transmission media includes coaxial cables, copper wire and fiber optics, including the wires that make up the bus 112. Transmission media also may also take the form of acoustic or light waves, such as those generated during radio wave and infrared data communications.

Various forms of computer readable media may be involved in carrying out one or more sequences of one or more instructions to processor 113 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 111 may receive the data on the telephone line and use an infrared transmitter to convert the data to an infrared signal. An infrared detector coupled to the bus 112 can receive the data carried in the infrared signal and place the data on the bus 112. The bus 112 carries the data to the main memory 114, from which the processor 113 retrieves and executes the instructions. The instructions received by the main memory 114 may optionally be stored on storage device 117 or 118 either before or after execution by processor 113.

The computer system 111 also includes at least one communication interface 123 (e.g. modem, telecom access card, etc) coupled to the bus 112. A communication interface 123 may provide a two-way data communication coupling to a network link 124 that is connected to, for example, a local area network (LAN) 125, or to another communications network 126 such as the Internet. The communication interface 123 may also include or serve as a telecom access device (e.g. if the communication interface is a telecom board), thus enabling the computer to act as an IVR (Interactive Voice Response) system. One non-limiting example of such telecom access hardware is commercially available from Dialogic, for example the Dialogic 480JCT board. Further, the communication interface 123 may be a network interface card to attach to any packet switched LAN. As another example, the communication interfaces 123 may be an asymmetrical digital subscriber line (ADSL) card, an integrated services digital network (ISDN) card or a modem to provide a data communication connection to a corresponding type of communications line. Wireless links may also be implemented. In any such implementation, the communication interfaces 123 may send and receive electrical, electromagnetic or optical signals that carry digital data streams representing various types of information.

The network link 124 typically provides data communication through one or more networks to other data or telecom devices. For example, the network link 124 may provide a connection to another computer or remotely located presentation device through a local network 125 (e.g., a LAN) or through equipment operated by a service provider, which provides communication services through a communications network 126. In preferred embodiments, the local network 124 and the communications network 126 preferably use electrical, electromagnetic, or optical signals that carry digital data streams. The signals through the various networks and the signals on the network link 124 and through the communication interface 123, which carry the digital data to and from the computer system 111, are exemplary forms of carrier waves transporting the information. The computer system 111 can transmit and receive data, including program code, through the network(s) 125 and 126, the network link 124 and the communication interface 123. Moreover, the network link 124 may provide a connection through a LAN 125 to a mobile device 127 such as a personal digital assistant (PDA) laptop computer, or cellular telephone. The LAN communications network 125 and the communications network 126 both use electrical, electromagnetic or optical signals that carry digital data streams. The signals through the various networks and the signals on the network link 124 and through the communication interface 123, which carry the digital data to and from the system 111, are exemplary forms of carrier waves transporting the information. The processor system 111 can transmit notifications and receive data, including program code, through the network(s), the network link 124 and the communication interface 123.

The exemplary embodiments below may use Interactive Voice Response (IVR) systems. IVR systems may be computing devices which can: answer phone calls; play audio to the caller during a phone call, such as "Please enter your ID number"; and accept input from the caller, for example, via touchtone input or speech input and the like where the caller operates a telephone to signal to the IVR system. By playing audio to a caller and accepting input from the caller, the IVR system conducts a dialog.

Current IVR systems can include computers that can communicate with phone callers via a wide variety of telecom transmission protocols. Telecom protocols selected sometimes, but not always, require that the computer contain a special physical telecom access card, similar to a modem, for connecting to telecom systems and communicating audio via a telecom transmission protocol. Some new digital protocols, such as the Voice over Internet Protocol (VoIP), do not require a special additional modem-like communication subsystem, but may have a communication device that can access a data network (a data card) and may use a program to control VoIP telecom calls. More traditional telephony systems and protocols typically are connected to and controlled by commercially available telecom access cards.

Telecom access cards are specifically designed to enable the computer to connect to a telecom system and contain means to allow the computer to programmatically control a dialog with one or more human beings on the other end of telecommunications connections (i.e., during phone calls). Telecom cards are commercially available such that, when installed in a computer, the computer can connect to and control voice calls over a variety of telecom protocols, including: analog lines, TDM digital lines, ISDN digital lines, Voice over IP lines, etc. Thus, exemplary embodiments of the below invention may use any of the telecom protocols and configurations described above.

In general, FIGS. 2-8 are directed to aspects of at least one exemplary embodiment of a method, system and apparatus for administering medicaments to patients where the medicaments are dispensed in a controlled fashion from a dispensing device. Although many steps are described as being performed by computer logic, a person of ordinary skill in the art will understand that one or more of these steps can be performed by a human being. For example, a human being can answer a phone call from a user, request identifying data, determine whether authorization to a dispensing device is advisable, relay access authorization data to the user for accessing medicaments housed in a dispensing device, and the like.

According to at least one exemplary embodiment, a method and system of managing access to medicaments can communicate limited-use access authorization data to a user of the drug dispensing device. The dispensing device can, in turn, utilize limited-use access authorization data to control access to medicaments. Embodiments can include using any dispensing device that supports the utilization of limited-use access authorization data (e.g., a single-use passcode) to gain limited access to the medicaments within the dispensing device.

The term "access authorization data" is used throughout, and passcodes are but one example of such data. Valid passcodes are used in at least one exemplary embodiment to indicate to the drug dispensing device that access to some amount of medicaments has been authorized.

An important aspect of at least one exemplary embodiment can be considered to be the use of controlled communication of limited-use access authorization data where such access authorization data (a non-limiting example being a passcode) can then be used to enable limited access to medicaments in a drug dispensing device. Hence, control over communication of valid access authorization data to a user of the dispensing device enables effective proxy control over ongoing access to medicaments in the medicaments in that dispensing device. Access to medicaments can be granted for limited use (e.g., the drug dispensing device only dispenses a certain quantity and/or dispenses over a certain period of time during which the passcode is valid) and at some point the access authorization data can expire. Thereafter, use of that access authorization data can fail to facilitate access to the medicaments in the drug dispensing device.

The access authorization data can be made to expire for any number of reasons, such as if the medicaments are accessed too often within a limited period of time. Once the access authorization data expires and is no longer valid, a user seeking access to further medicaments can seek new access authorization data (e.g. a new passcode) from an external resource (e.g. an external interfacing server via a communicative intermediary). If new access authorization data is not sought, the user can be left without the ability to access the medicaments within the drug dispensing device. If the user requests new and valid access authorization data, this access data can be provided if the logic of the system controlling communication of the access authorization data deems it proper to do so. In at least one exemplary embodiment, the user is asked for identifying data as a necessary step before the user can potentially receive new access authorization data. The identifying data provided can be evaluated and conclusions derived from the identifying data may affect whether to provide new valid access authorization data, or which access authorization data to provide, and selective denial of access authorization data is a possibility in at least one exemplary embodiment.

The phrase "identifying data" is used throughout, and identifying data can include one or more items such as a device identification number or name, device status information, a user name, a user identification number, a treatment identification number, treatment description, data about the medicament prescription, and similar data known to one having ordinary skill in the art. In particular, the identifying data could include information displayed on the device such as a status code that can be used to derive further information about the quantity and/or pattern of access to the medicaments during the intervening time since the last communication with the user.

In at least one exemplary embodiment, the control of communicating valid access authorization data can be achieved by requiring a person (typically the user of the medicaments) to input identifying data to an interfacing server via a communicative intermediary before providing the user with valid access authorization data. A determination can then be made as to whether or not it is advisable to provide valid access authorization data thereafter. In at least one exemplary embodiment, the identifying data collected contains information about the history of medicament access, and this data can be used in a process to determine whether or not it is advisable to provide further access authorization data. In at least one other exemplary embodiment, no direct data about device dispensing history is collected as part of identifying data, but rather the time at which the user seeks access is used to infer whether the user is or is not complying with an acceptable treatment regimen, and based on this access authorization data is confirmed on denied.

The determination of whether access authorization data should be communicated to the user can be made programmatically, and the program can incorporate any algorithm/logic conceived to decide whether or not access should be authorized. Medical considerations that may be taken into account include concerns that the patient may be dispensing medicaments too frequently, and thus may be exhibiting signs of drug addiction (and therefore medicament access should be curtailed). Also, the patient may not be taking the medicament at the right time to maximize the effectiveness of the medicament and access authorization data can be withheld until the appropriate time. The inputs to the determination could include data about when the user has sought access to medicaments in the past.

In at least one other exemplary embodiment, the dispensing device can be programmed by one with ordinary skill in the art to log the times at which medicaments were accessed in the device. This log data, or the most relevant information in this log, can be communicated by the user as identifying data. At least one exemplary embodiment described herein assumes that the time of dispensing is close to the time of the last communication of valid access authorization data. It is possible for one skilled in the art to identify and create a wide variety of dispensers that are amenable to this tracking. A wide variety of sub systems can be conceived of that track when medicaments were removed from a dispenser, as will be known to one with ordinary skill in the art (e.g. a tray that rotates to reveals a pill in a discrete compartment, whereby that rotation can be monitored; A dispenser that pushes pills out from a cartridge, whereby that removal from a cartridge can be monitored; Or an electro-optical detector that 'sees' when a pill is removed from a dispenser).

Data collected by the device about the times of medicament access can condensed and encoded into a form, such as a status code, that could be communicated easily as by the user identifying data. As one non-limiting example, if the dispensing device is programmed to limit usage to no more than three pills during a 48 hour period, the status code for such as 48 hour period could be designed as three 2-digit numbers conjoined, each 2-digit number indicating the hour at which a medicament was dispensed during that 48 hour window. Status code 04 14 36 would indicate that pills were dispensed at hours 4, 14, and 36, while 05 05 00 would indicate that two pills were dispensed during hour 5 and none thereafter.

Various types of information collected by the dispensing device, including device status and dispensing history information, could be requested during any dialog with a user of the device. Anyone skilled at the art could conceive of a variety of information that the dispensing device could log, and that a user could communicate, as part of identifying data.

In at least one exemplary embodiment, the determination of whether or to provide access authorization data can include an algorithm that checks to see if sufficient time has passed since the last access authorization data was supplied. Such a relatively simple algorithm can be useful in controlling access to an addictive medicament, but the simplicity of this exemplary algorithm is not intended to be limiting.

In at least one other exemplary embodiment, access authorization data is always communicated upon receipt of valid identifying data. While this embodiment does not necessarily limit access to medicaments dispensed, it nonetheless enables remote monitoring of the pattern of medicament access, and could provide a process for collecting a variety of identifying data from a user.

In addition to controlling and tracking access to medicaments in a dispensing device, various embodiments also serve as a practical mechanism for gathering information about when to remind users to take medicaments. In general, if a user fails to seek access authorization data within expected time expected, users are not following a treatment regimen in an appropriate manner. Anyone skilled in the art can act on this inferred data to remind the user to do so by employing various types of reminder systems. Thus, at least one exemplary embodiment can remind the user to take the medicament if it can be inferred that they have not done so within a prescribed time frame.

Figure 2:
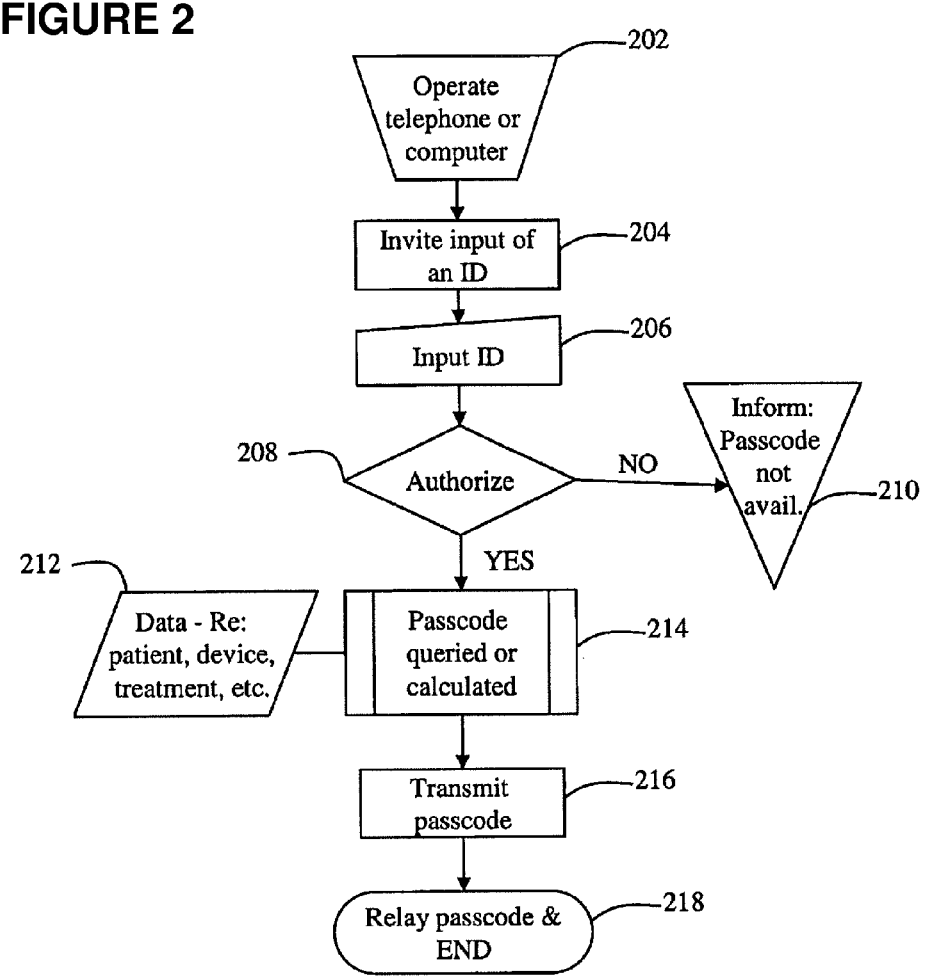
FIG. 2 is a flowchart showing an exemplary process for providing access authorization data via an interfacing system.

Referring to FIG. 2, a process for accessing a medicament (or predetermined dosage quantity thereof) where a patient can receive access authorization data such as a passcode or password for operating a medicament dispensing device is shown in accordance with at least one exemplary embodiment of the present invention. In at least one exemplary embodiment, the access authorization data can be limited-use access authorization data such as single-use (i.e. "one-time") access authorization data. For instance, single-use access authorization data (a species of limited-use access authorization data) can require a patient to request subsequent single-use access authorization data after the current single-use access authorization data has expired, for example, through a one-time use with the dispensing device and/or through the expiration of the designated time period for use.

Limited-use access can describe access to a certain quantity of medicaments (or dosages thereof) or can describe access to any number of medicaments over a range of time. Also, limited-use access can describe access to a certain quantity over a certain period of time. As such, limited-use access authorization data is intended to be broadly interpreted as information that can be used to provide access to medicaments based on limiting criteria. Limited-use access authorization data can provide access to a certain quantity of doses of a medicament or can provide access to medicaments over a certain period of time and any combination thereof (e.g., a limited-use passcode can be used up to three times during the next forty-eight hour period and thereafter the passcode will expire). After the limit of use has been reached, the limited-use access authorization data will no longer enable access to medicaments.

Thus, the process shown in FIG. 2 can be repeated each time a patient requests access authorization data for dispensing a medicament and limited-use access authorization data can be provided each time it is determined to be medically advisable to provide such access authorization data. Exemplary embodiments are sometimes described herein with reference to single-use access authorization data such as a single-use passcode. This is intended to be merely illustrative and not limiting as one of ordinary skill in the art will appreciate that limited-use access authorization data can be accommodated. In other words, exemplary embodiments referring to single-use access authorization data can make use of limited-use access authorization data to also provide access to two or more doses of medicaments. Hence exemplary embodiments making reference to single-use access authorization data can also serve as a guide to someone with ordinary skill in the art to create exemplary embodiments utilizing limited-use access to any arbitrary quantity of medicaments. In effect, all references herein to single-use access authorization data can be broadened and generalized as limited-use access authorization data. Limited use can be interpreted as open access to medicaments over any arbitrary quantity of time, or for any quantity over any period of time as well.

Still referring to FIG. 2, at step 202, a patient (or a person acting on behalf thereof) can operate a communicative intermediary such as a telephone and like devices having telephone functionality to interface with an interfacing system (e.g., a "remote master system") such as an IVR system. Alternatively, a patient can operate a personal computing device such as a computer having webpage browsing capability to view a webpage requested from a web server that provides a means for inputting identifying data such as an identification number for the dispensing device (which may also function as a patient identification number or be associated therewith), as shown in step 204. Other non-limiting examples of identifying data may be a status code displayed on the device, prescription identification, etc. Moreover, in web-based embodiments, a secured Internet connection may be used, as is well known in the art.

In other embodiments, the communicative intermediary can be a device with text messaging functionality and the interfacing system can be one that can process text messages as one more non-limiting example. For example, a patient can transmit identifying data in text form over a mobile phone telecom system (e.g. "text message", such as in "texting information to a five-digit short code" as is known in the art, and similar to "email"). Another communicative intermediary could be an email system.

At step 204, the communicative intermediary can act to prompt a patient to input the identifying data. For example, embodiments having an IVR system can initiate a dialog and make audio requests through a telephone such as: "Please enter your identification number," or "Please enter your device ID number", or "Please enter the status code displayed on your device", and the like. Similarly, web-based embodiments can invite a patient to input the identifying data by providing a webpage having a portion for inputting the identifying data. For instance, a webpage can have a graphical user interface (GUI) widget such as a textbox for entering the identifying data.

In at least one exemplary embodiment, identifying data can include a device identification ("device ID") number. That device can be associated in a database with a certain active patient and a certain active treatment regimen. If the device ID number is the identifying data, then a database (described below) can store an association between the device ID and the patient in possession of that device, information about the medicaments in that device, information about the treatment regimen associated with that treatment and the like.

Nevertheless, identifying data can include any information known to one with skill in the art, such as information that enables identification of the device, identification of the patient, identification of the device status, identification of the device dispensing history, identification of the treatment regimen, any form of information about the quantity and times at which medicaments were dispensed from the device, etc. And identifying data could also be supplemented by a question and answer dialog, where the user responds with information that could be medically useful, such as information about pain levels, symptoms, etc. This identifying data serves as the key input to an algorithm for determining whether, when, and or which access authorization data should be allowed to be delivered to the user.

After a patient inputs identifying data at step 206, the inputted identifying data can be received at the interfacing computer system. At step 208, the interfacing computer system can request authorization from a storage server system (i.e. which may be referred to as a "master medical system"), which may be a database system having a database storing (and associating) data 212 such as patient biographical data, device data including device identification data and device status data, medical/treatment data pertaining to patients and their prescribed medicament regimens, access authorization data (including, e.g., passcodes, passcode algorithms and the like), stored procedures for interpreting device status data, and the like known to one having ordinary skill in the art (see, e.g., FIG. 4). As one non-limiting example, the database can be a relational database.

Notably, the interfacing and storage systems can be viewed as integral parts of an authorizing system including both operatively connected in accordance with at least one exemplary embodiment. The interfacing and storage systems can be implemented on a single computer, a central computer system or distributed.

In at least one exemplary embodiment, the interfacing server can collect identifying information from the caller and transmit that data to the storage system. The storage system can process the identifying data and can execute algorithms to determine whether it is medically advisable to provide a medicament (or predetermined dosage quantity thereof) to the patient associated with the identifying data based on, for example, the treatment data stored within the storage system (e.g., a database thereof) and decision logic configured to process such data.

As will be readily understood by one having ordinary skill in the art, the determination of whether it is medically advisable to provide a medicament can be based on the timing and dosage criteria of the treatment regimen prescribed for the medicament in conjunction with inferred information about medicament access derived from the techniques set forth herein. Such a decision can factor in data such as the last and previous outputs of access authorization data to the patient, which can be recorded within the storage system, and any other device status information or patient information reported during the dialogue with the user. In the absence of detailed device status data, outputs of access authorization data can be considered evidence that the patient actually received their medicament dosage proximate the time the access authorization was requested. Overall, the storage system can be used to track a patient's compliance with the prescribed treatment regimen as well as track various other indicators related to a patient's health.

If it is determined to be medically advisable to deny the patient access to the medicament, then the storage system can transmit a denial to the interfacing system, alerting it that access authorization data is not available for providing to the patient. At step 210, the interfacing system can alert the patient (or a person acting on behalf thereof) that the access authorization data is not available (or accessible) at this time through the communicative intermediary. For example, an audio message in embodiments having an IVR system can be played alerting of such or, alternatively, in web-based embodiments, a webpage showing that the request for access authorization data has been denied and that the access authorization is not available can be displayed to a user of a computing device.

If it is determined to be medically advisable to provide the patient with access to the medicament according to the decision logic, then the storage system can transmit an authorization to the interfacing system to provide the requested access authorization data, which can be limited-use access authorization data such as a passcode, password, visual ticket and the like known to one having ordinary skill in the art. Upon authorization, the interfacing system can compute or retrieve from the storage system the access authorization data at step 214. For example, the interfacing system can compute or retrieve single-use access authorization data, such as a passcode based on a predetermined algorithm (or any known type of random number generator), for generating seemingly random single-use passcodes.

Alternatively, a password generator can be used as the generator for single-use passwords as one more non-limiting example. Exemplary embodiments described herein will generally be described in reference to passcodes, algorithms and random number generators, which is illustrative and not intended to be limiting as will be appreciated by one having ordinary skill in the art.

Still referring to FIG. 2, for example, a database of the storage system can store the algorithm where the interfacing system can query the algorithm and calculate the passcode. Alternatively, at step 214, the access authorization data itself can be queried from a database on the storage system where sets of access authorization data pertaining to each patient are stored for providing limited-use access authorization data in response to a patient's request. For example, the known results of a calculated passcode pattern for providing single-use passcodes can be stored in the database.

In at least one exemplary embodiment, if the patient fails to seek access authorization data for the dispensing device within a predetermined time period or around a prescribed time, the interfacing system or another system may alert the patient or a contact person (e.g., guardian, caregiver, relative, etc.) of the need to request access authorization data. These alerts can be of any type known to one having ordinary skill in the art including, for example, alerts transmitted through phone calls, text messages, emails and audible and/or visual alarms. These alerts can also be communicated directly to the patient via the dispensing device. In at least one exemplary embodiment, the device may begin making a beeping sound when the limit of use has been reach. This will serve to remind the patient to take action, which could include the action of checking in to provide identifying data and receive new access authorization data. In at least one exemplary embodiment, this reminder capability is provided instead of providing a locking mechanism that prevents access to the medicaments. The reminder system, implemented by a beeping sound that continues until the patient inputs new valid access authorization data, stimulates the act of checking in by proving to be an annoyance to the patient. This reminder system can also be combined with the teachings herein for providing a locking mechanism on the device, and reminders can be programmatically designed to begin prior to the locking of the device. For example a reminder beep might begin 24 hours prior to the locking of the system implied by the limit of use associated with the initial access authorization data. Hence the beeping would remind the patient to seek a new access authorization code prior to full lock. In another exemplary embodiment, one skilled in the art to use the principles described herein to create a medication management system that does not employ a lock on the medication dispenser, but instead employs limited use access authorization data that along with reminders that are initiated at the conclusion of that limit of use. This system might be preferable for use with medications where locking the patient out for the medicaments is deemed undesirable, yet a mechanism is still required to stimulate regular patient check-in and collection of identifying data.

Also, in at least one exemplary embodiment, an alert can be transmitted to other parties including caregivers, family, or medical professionals such as doctors and pharmacists or their respective staff, that alert indicating to these parties that some sort of patient issue has been detected via the communication with the user described herein. The alert transmission to such parties can be made through the storage system or, alternatively, through the interfacing system as well as any other suitable system connected therewith. In particular, in at least one exemplary embodiment, an alert can be sent to interested parties if the patient is seeking access to a medicament in a pattern determined to be suggestive of addiction, abuse, misuse and the like.

At step 216, the interfacing system can transmit the limited-use access authorization data, which may be single-use access authorization data, to the communicative intermediary. At step 218, the communicative intermediary can relay the access authorization data to the patient (or a person acting on behalf thereof). For example, an audio message in embodiments having an IVR system can be played relaying the access authorization data to the telephone user or, alternatively, in web-based embodiments, a webpage showing the access authorization data can be displayed on the computing device of the user.

In relation to the process of FIG. 2, one exemplary embodiment can include server code implemented to allow an IVR system to interact with a patient and provide, for example, a current passcode.

Exemplary code is provided herein for an exemplary embodiment that uses an IVR system. This exemplary code consists of PHP scripts, a common scripting language widely used by programmers skilled in the art of web programming, and VoiceXML code, a common scripting language widely used by programmers skilled in the art of IVR programming.

For instance, an exemplary code device configured to provide the basic IVR system menu can include:

```
<?php
header("Content-type: text/xml");
echo("<?xml version=\"1.0\"?>");
?>
<vxml version="2.1">
<property name="inputmodes" value="dtmf"/>
<form id="mainmenu">
    <field name="menuchoice">
        <grammar type="application/x-jsgf">1|2|0</grammar>
        <prompt>
            Welcome to the Medica Safe access line.
            To receive a new passcode
            for your Medica Safe, press 1.
                If you would like to be reminded of
                your current passcode again, press 2.
        </prompt>
        <filled>
            <if cond="menuchoice==0">
                <goto next="#support"/>
            </if>
        </filled>
    </field>
    <subdialog name="result" src="#get_device_id">
        <filled>
            <var name="v_device_id" expr="result.device_id"/>
            <if cond="menuchoice==1">
                <submit next="ms1_request_new_code.php"
                    namelist="v_device_id" method="post"/>
            <elseif cond="menuchoice==2"/>
                <submit next="ms1_read_current_code.php"
                    namelist="v_device_id" method="post"/>
            </if>
        </filled>
    </subdialog>
</form>
<!-- subdialog to get device Id number -->
<form id="get_device_id">
    <field name="device_id" type="digits">
        <prompt>
            Please enter the device ID located on your
            Medica Safe device, followed by the pound sign.
        </prompt>
        <filled>
            <return namelist="device_id"/>
        </filled>
    </field>
</form>
<form id="support">
    <field name="waitforsupport" type="digits">
        <grammar type="application/x-jsgf">1|2</grammar>
        <prompt>
```

The wait to speak with a support person is approximately 10 minutes. If all you need to do is get a new passcode to access pills in your Medica Safe device, we suggest that you press 1 and we will direct you into the automated system for new pass codes. You will be asked one key question, namely the device number which you will find printed on the back of your Medica Safe device. Then the system will give you a valid passcode if you are currently authorized to take this medication.

At times, callers do not hear their passcode correctly. If you would like to have your current passcode repeated, press 2 now.

If you have already received the passcode, or are unable to access you passcode and suspect there is an error, please feel free to wait on the line for a live operator."

```
        </prompt>
        <filled>
         <if cond="waitforsupport==1">
               <goto next="ms1_request_new_code.php"/>
            <elseif cond="waitforsupport==2"/>
               <goto next="ms1_read_current_code.php"/>
            </if>
        </filled>
      </field>
    </form>
  </vxml>
```

Also, an exemplary code device configured to enable a caller to request a new passcode (where authorization is provided via a storage system having a database) can include:

```
<?php
header("Content-type: text/xml");
echo("<?xml version=\"1.0\"?>");
include_once("lib/dbaccess.php");
db_ms1_connect( )
?>
<vxml version="2.1">
<property name="inputmodes" value="dtmf"/>
<?php
if (isset($_POST["v_device_id"]))
{
        $device_id = $_POST["v_device_id"];
        $query="SELECT * FROM Treatment_Info WHERE (FK_Device_ID =
        '$device_id' AND StillActive = '1')";
        $result = mysql_query($query);
        if (mysql_numrows($result)==0)
        {
                echo <<<END
                <form>
                  <block>
                    <prompt>
                    The system does not recognize that Device ID.
                    You entered <say-as type="acronym">$device_id</say-as>.
You should have entered the device ID
                        printed on your device.
                        The system will now return to the main menu.
                    </prompt>
                    <goto next="ms1_intro.php"/>");
                  </block>
                </form>
END;
        } else {
                $treatment_id = mysql_result($result,0,"Treatment_ID");
                $time_nextaccess = mysql_result($result,0,"Time_NextAccess");
                $minimum_timediff = mysql_result
($result,0,"Minimum_Interval");
                $patient_id = mysql_result ($result,0,"FK_Patient_ID");
                $treatment_type = mysql_result ($result,0,"Treatment_Type");
                $query= "SELECT * FROM Device_Info WHERE (Device_ID =
'$device_id')";
                $result = mysql_query($query);
                $passcode_rank =
mysql_result($result,0,"Passcode_CurrentRank");
                $old_passcode = mysql_result($result,0,"Passcode_Current");
                $now = Time( );
                if ($now > $time_nextaccess)
                {
                        $result = mysql_query("SELECT * FROM Algorithm1");
                        $num_rows = mysql_num_rows($result);
                        ++$passcode_rank;
                        if (($num_rows)<($passcode_rank))
                        {
                                $passcode_rank=1;
                        }
                        $query= "SELECT * FROM Algorithm1 WHERE
                                (Passcode_Rank = '$passcode_rank')";
                        $result = mysql_query($query);
                        $new_passcode = mysql_result($result,0,"Passcode");
                        $query= "UPDATE Device_Info SET
```

```
Passcode_Current='$new_passcode',
                        Passcode_Past = '$old_passcode', Passcode_CurrentRank=
'$passcode_rank'
                        WHERE Device_ID = '$device_id' ";
                        $result = mysql_query($query);
                        $query = "INSERT INTO Patient_Sessions
                        (FK_Treatment_ID,FK_Device_ID,FK_Patient_ID,
TimeStamp,StatusCode,
                        Passcode_Given, Passcode_GivenPrevious) VALUES
        ('$treatment_id','$device_id','$patient_id','$now','0','$new_passcode',
'$old_passcode')";
                        mysql_query($query);
                        $time_nextaccess = ($now + $minimum_timediff);
                        $query= "UPDATE Treatment_Info SET
Time_NextAccess='$time_nextaccess'
                         WHERE (Treatment_ID = '$treatment_id') ";
                         $result = mysql_query($query);
                        ECHO <<<END
                        <form id="state_passcode">
                          <field name="menuchoice">
                            <grammar type="application/x-jsgf">1|2</grammar>
                                <prompt> Your new passcode is <say-as
type="acronym">$new_passcode</say-as>.
                                Again, your new passcode is <say-as
type="acronym">$new_passcode</say-as>.
                                To repeat this information again, press 1.
                                To return to the main menu, press 2.
                                </prompt>
                            <filled>
                                <if cond="menuchoice==1">
                                <goto next="#state_passcode"/>
                                <elseif cond="menuchoice==2"/>
                                <goto next="ms1_intro.php"/>
                                </if>
                            </filled>
                          </field>
                        </form>
END;
                } else {
                        $time_required = ($time_nextaccess – $now);
                        $hours_required = floor($time_required/3600);
                        $minutes_required = ((floor($time_required/60))%60);
                         echo <<<END
                        <form id="call_back_when">
                          <field name="menuchoice">
                            <grammar type="application/x-jsgf">1|2</grammar>
                            <prompt>You cannot access a new passcode now.
                                You can get a new passcode in
END;
                        echo ("$hours_required hours and $minutes_required
minutes.");
                         echo <<<END
                        Your last passcode was <say-as
type="acronym">$old_passcode.</say-as>
                        If you have already used that last passcode, it will no
longer work.
                        To repeat, your last passcode was <say-as
type="acronym">$old_passcode.</say-as>
                        To repeat this information again, press 1.
                        To return to the main menu, press 2.
                        </prompt>
                        <filled>
                                <if cond="menuchoice==1">
                                <goto next="#call_back_when"/>
                                <elseif cond="menuchoice==2"/>
                                <goto next="ms1_intro.php"/>
                                </if>
                            </filled>
                          </field>
                        </form>
END;
                }
        }
```

```
} else {
echo <<<END
<form>
   <block>
      <prompt>
         You should have entered your device id,as printed on
         on your device The system will now return to the main menu.
      </prompt>
      <goto next="ms1_intro.php"/>
   </block>
</form>
END;
}
mysql_close( );
?>
</vxml>
```

Moreover, embodiments of the present invention can include an exemplary code device configured to remind a caller of their current passcode if forgotten, which can include:

```
<?php
header("Content-type: text/xml");
echo("<?xml version=\"1.0\"?>");
include_once("lib/dbaccess.php");
db_ms1_connect( )
?>
<vxml version="2.1">
<property name="inputmodes" value="dtmf"/>
<?php
if (isset($_POST["v_device_id"]))
{
          $device_id = $_POST["v_device_id"];
          $query="SELECT * FROM Treatment_Info WHERE (FK_Device_ID =
          '$device_id' AND StillActive = '1')";
          $result = mysql_query($query);
          if (mysql_numrows($result)==0)
          {
                    echo <<<END
                    <form>
                       <block>
                          <prompt>
                          The system does not recognize that Device ID.
                          You entered <say-as type="acronym"> $device_id </say-as>.
You should have entered the device ID
                          printed on your device.
                          The system will now return to the main menu.
                          </prompt>
                          <goto next="ms1_intro.php"/>");
                       </block>
                    </form>
END;
          } else {
                    $treatment_id = mysql_result($result,0,"Treatment_ID");
                    $time_nextaccess = mysql_result($result,0,"Time_NextAccess");
                    $minimum_timediff = mysql_result
($result,0,"Minimum_Interval");
                    $patient_id = mysql_result ($result,0,"FK_Patient_ID");
                    $treatment_type = mysql_result ($result,0,"Treatment_Type");
                    $query= "SELECT * FROM Device_Info WHERE (Device_ID =
'$device_id')";
                    $result = mysql_query($query);
                    $passcode_rank =
mysql_result($result,0,"Passcode_CurrentRank");
                    $old_passcode = mysql_result($result,0,"Passcode_Current");
                    $now = Time( );
                    $time_required = ($time_nextaccess - $now);
                    if ($time_required <= 0 ) {
                                  $time_required=0;
                    }
                    $hours_required = floor($time_required/3600);
                    $minutes_required = ((floor($time_required/60))%60);
                    echo <<<END
                    <form id="call_back_when">
                       <field name="menuchoice">
```

-continued

```
            <grammar type="application/x-jsgf">1|2</grammar>
            <prompt>
                Your last passcode was <say-as type="acronym">$old_passcode</say-as>.
                If you have already used that last passcode, it will no longer work.
                To repeat, your last passcode was <say-as type="acronym">$old_passcode</say-as>.
                You can get a new passcode in
END;
                echo ("$hours_required hours and $minutes_required minutes.");
                echo <<<END
                To repeat, your last passcode was <say-as type="acronym">$old_passcode.</say-as>
                To repeat this information again, press 1.
                To return to the main menu, press 2.
            </prompt>
            <filled>
                <if cond="menuchoice==1">
                <goto next="#call_back_when"/>
                <elseif cond="menuchoice==2"/>
                <goto next="ms1_intro.php"/>
                </if>
            </filled>
        </field>
    </form>
END;
        }
} else {
echo <<<END
<form>
    <block>
        <prompt>
            You should have entered your device id,as printed on
            on your device The system will now return to the main menu.
        </prompt>
        <goto next="ms1_intro.php"/>
    </block>
</form>
END;
}
mysql_close( );
?>
</vxml>
```

Figure 3:
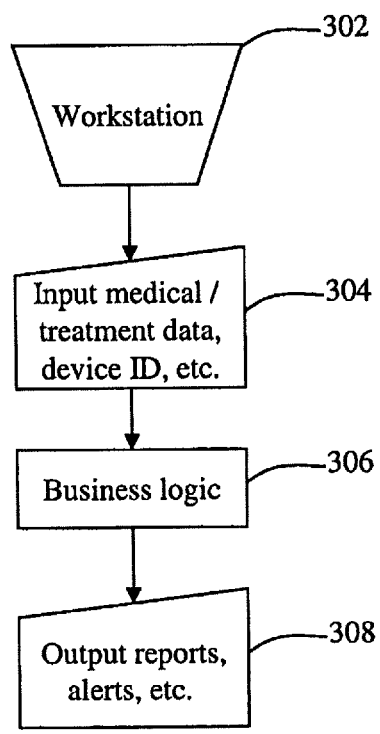
FIG. 3 is a flowchart showing an exemplary process for a storage system.

Now referring to FIG. 3, a process for inputting data, such as patient biographical data, device data including device identification data, medical/treatment data pertaining to patients and their prescribed medicament regimens and the like, into a storage system (i.e. the medical master system) is shown in accordance with at least one exemplary embodiment of the present invention. At step 302, an operator can operate a terminal for a computing device for inputting such data into the storage system while, for example, at a workstation. The storage system can be remote and remotely accessible from the client computing device through a network such as the Internet.

The operator of such a computing device is envisioned, in accordance with at least one exemplary embodiment, to be an administrator for a medical provider. For example, the medical provider can be a hospital, a doctor's office, a pharmacy and the like. An administrator can be any medical professional such as a doctor, pharmacist, psychiatrist and the like, as well as any staff (e.g, a receptionist, nurse, technician, etc.), who also can be considered medical professionals depending on usage, working on behalf thereof. Also, in at least one exemplary embodiment, the administrator can be an employee of a healthcare insurance company and the like. Moreover, in at least one embodiment, it is envisioned that the operator will be the patient or a person acting on behalf thereof (e.g., guardian or caregiver) who is not an administrator for a medical provider or health insurance company.

Before inputting data at step 304, an operator may have to log in at step 302 to gain access to the storage system through any login means known to one having ordinary skill in the art. For example, logging in can be effectuated by providing a username and password to securely access the storage system via a secured Internet connection as is well known in the art. Customary procedures in the field of medical data can be used to determine the level of access granted to the operator.

Figure 4:
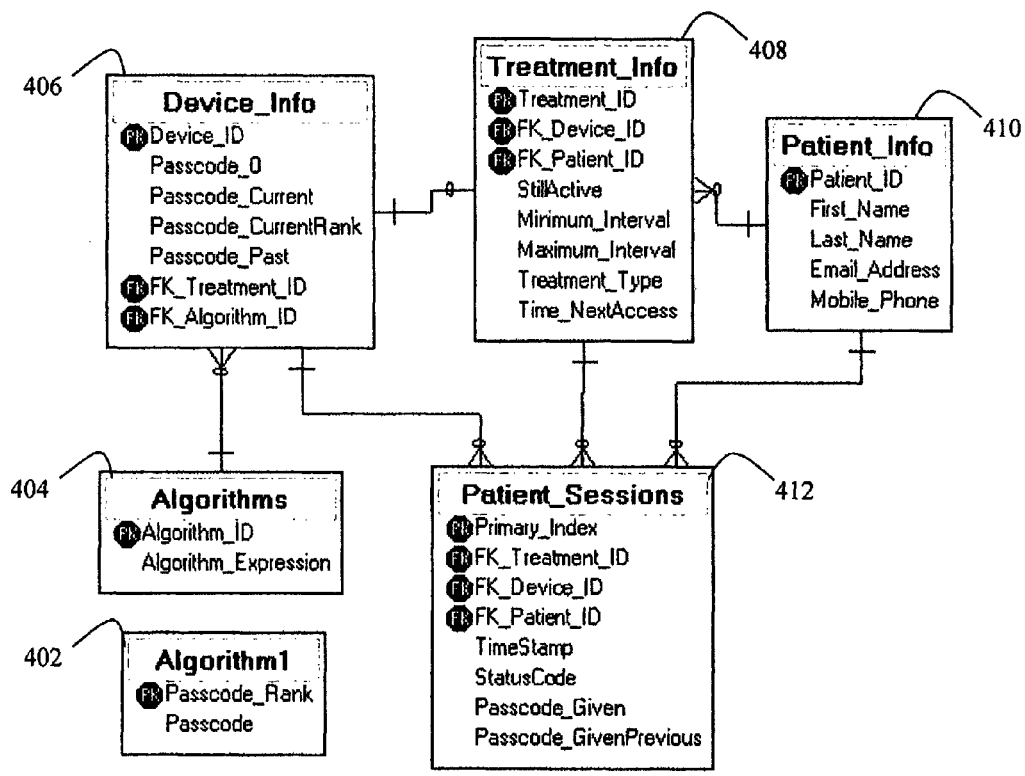
FIG. 4 is a database schema for an exemplary database implemented on a storage system.

At step 304, the operator can input data such as patient biographical data, device data including device identification data, medical/treatment data pertaining to patients and their prescribed medicament regimens and the like into the storage system, which can be stored and organized in a database (see, e.g., FIG. 4). As stated before, the storage system and any associated database can also include access authorization data and/or access authorization data algorithms for determining a limited-use access authorization data. The operator can input data via administrative screens for data entry such as webpage forms providing data entry means through GUI widgets.

For instance, during patient enrollment, the operator can enter needed patient biographical data, needed treatment/medical data including treatment regimen, the quantity of medicaments disposed within and housed by the dispensing device, dispensing device identification data (e.g., identification number) and the like known to one having ordinary skill in the art. Also, at this time, a patient can be provided with the medicament dispensing device as well as any needed information for contacting the interfacing system of an authorizing system (see, e.g., FIG. 2) in order to receive access authorization data such as a limited-use passcode for gaining access to a dosage of the medicaments.

For example, an exemplary code device for providing a web form for inputting data regarding a new dispensing device can include:

```
<?php
header("Content-type: text/html");
?>
<html>
    <head>
        <title>
Enter data to enroll a new device for the MedicaSafe system.
        </title>
    </head>
<?php
$db_host = "localhost";
$db_user = "root";
$db_pwd = "zbnm15";
$db_name = "db_ms1";
mysql_connect($db_host, $db_user, $db_pwd);
mysql_select_db($db_name);
?>
<body>
<?php
if (!isset ($_POST['submit'])) {
    ?>
    <form action="" method="post">
    Device ID Number: <input type="text" name="device_id"><br>
    Passcode 0: <input type="text" name="passcode_0"><br>
        Current Passcode: <input type="text" name="passcode_current"><br>
    Current Passcode Rank: <input type="text"
name="passcode_currentrank"><br>
        Algorithm ID: <input type="text" name="algorithm_id"><br>
        <input type="submit" name="submit" value="Submit!"
    </form>
    <?php
} else {
        $Device_ID = $_POST['device_id'];
        $Passcode_0 = $_POST['passcode_0'];
        $Passcode_Current = $_POST['passcode_current'];
        $Passcode_CurrentRank = $_POST['passcode_currentrank'];
        $Algorithm_ID = $_POST['algorithm_id'];
        $result=mysql_query("SELECT * FROM Device_Info WHERE (Device_ID =
'$Device_ID')");
        $number = mysql_num_rows($result);
        echo "$number";
        if ($number==0)
            {
            mysql_query("INSERT INTO Device_Info
            (Device_ID,Passcode_0,Passcode_Current, Passcode_CurrentRank,
            FK_Algorithm_ID) VALUES ('$Device_ID',
'$Passcode_0','$Passcode_Current','$Passcode_CurrentRank','$Algorithm_ID
')");
            echo "Adding a new device . . . ";
            }
        else
            {
            if (!mysql_query("
            UPDATE Device_Info SET
            Passcode_0='$Passcode_0',
            Passcode_Current='$Passcode_Current',
            Passcode_CurrentRank='$Passcode_CurrentRank',
            FK_Algorithm_ID='$Algorithm_ID'
            WHERE Device_ID='$Device_ID'
            ")) { die(mysql_error( ));}
            echo "Overiding data for existing device . . .";
            }
        $result = mysql_query("SELECT * FROM Device_Info WHERE
(Device_ID='$Device_ID')");
        $temp_passcode = mysql_result($result, 0,Passcode_Current);
        echo "Data for a New Device $Device_ID has been added with current
        passcode $temp_passcode.";
}
?>
</body>
</html>
```

Additionally, an exemplary code device for providing a web form for inputting patient-related data (which could be further customized by one with ordinary skill in the art to include additional patient biographical data, treatment/medical data including certain treatment regimen data, the quantity of medicaments disposed within and housed by the dispensing device, dispensing device identification data and the like) can include:

```
<?php
header("Content-type: text/html");
?>
<html>
    <head>
        <title>
Enter data to enroll a new treatment regimen for the MedicaSafe system
        </title>
    </head>
<?php
include_once("lib/dbaccess.php");
$temp=db_ms1_connect( );
?>
<body>
<?php
if (!isset ($_POST['submit'])) {
        ?>
        <form action="" method="post">
        Patient_ID (leave blank if new patient): <input type="text" name="patient_id"><br>
            First Name: <input type="text" name="first_name"><br>
            Last Name: <input type="text" name="last_name"><br>
            Mobile Phone: <input type="text" name="mobile_phone"><br>
            Email Address: <input type="text" name="email_address"><br>
            Device ID Number: <input type="integer" name="device_id"><br>
            [Optional]Past Passcode: <input type="text" name="passcode_past"><br>
            [Optional]Treatment Type: <input type="text" name="treatment_type"><br>
            Minimum Interval(minutes): <input type="text" name="minimum_interval"><br>
            Maximum Interval(minutes): <input type="text" name="maximum_interval"><br>
            <br>
            <input type="submit" name="submit" value="Submit!">
        </form>
        <?php
        } else
{
$Patient_ID = $_POST['patient_id'];
$First_Name= $_POST['first_name'];
$Last_Name = $_POST['last_name'];
$Mobile_Phone = $_POST['mobile_phone'];
$Email_Address = $_POST['email_address'];
$Device_ID = $_POST['device_id'];
$Passcode_Past = $_POST['passcode_past'];
$Treatment_Type = $_POST['treatment_type'];
$Minimum_Interval = (60*($_POST['minimum_interval']));
$Maximum_Interval = (60*($_POST['maximum_interval']));
$StillActive = TRUE;
$query= "SELECT * FROM Device_Info WHERE (Device_ID = '$Device_ID')";
$result = mysql_query($query);
if (!mysql_num_rows($result))
{exit ( "There is no device registered with this Device ID number yet.");}
$Result = mysql_query("SELECT * FROM Patient_Info WHERE
First_Name='$First_Name' AND Last_Name ='$Last_Name'");
if ((mysql_num_rows($Result) ==0)) {
        mysql_query("INSERT INTO Patient_Info (First_Name, Last_Name,
        Mobile_Phone, Email_Address) VALUES ('$First_Name',
'$Last_Name','$Mobile_Phone','$Email_Address')");
            $query = "SELECT Patient_ID FROM Patient_Info WHERE
First_Name='$First_Name' AND Last_Name = '$Last_Name'";
            $result = mysql_query ($query);
            $Patient_ID = mysql_result($result,0,"Patient_ID");
            echo "A New Patient has been created with ID $Patient_ID.";
        }
        else
        {
        $query = "SELECT Patient_ID FROM Patient_Info WHERE
(First_Name='$First_Name' AND Last_Name = '$Last_Name')";
            $result = mysql_query ($query);
            $Patient_ID = mysql_result($result,0,"Patient_ID");
            $query = "UPDATE Patient_Info SET Mobile_Phone = '$Mobile_Phone',
                Email_Address='$Email_Address' WHERE (First_Name =
'$First_Name' AND Last_Name='$Last_Name')" ;
            mysql_query($query);
```

```
            echo "The patient already had a Patient_ID of $Patient_ID. Mobile
number and email address have been updated.";
            }
            $now=Time( );
            $query = "UPDATE Treatment_Info SET StillActive= '0' WHERE
FK_Device_ID='$Device_ID'";
            mysql_query ($query);
            $query = "INSERT INTO Treatment_Info (FK_Device_ID,
FK_Patient_ID,StillActive, Minimum_Interval, Maximum_Interval,Treatment_Type,
Time_NextAccess)
            VALUES
            ('$Device_ID','$Patient_ID','$StillActive','$Minimum_Interval','$Maximum_Inter-
val
', '$Treatment_Type','$now')";
            $result = mysql_query ($query);
            $query = "SELECT * FROM Treatment_Info
            WHERE (FK_Patient_ID='$Patient_ID' AND FK_Device_ID = '$Device_ID' AND
StillActive = '1')";
            $result = mysql_query ($query);
            $Treatment_ID = mysql_result($result,0,"Treatment_ID");
            echo "The treatment information has been inserted with Treatment ID of
$Treatment_ID.";
mysql_close( );
}
?>
</body>
</html>
```

Still referring to FIG. 3, at step 306, the storage system (medical master system) can have customary procedures in the field of data processing configured to process the data (e.g., that data including device and patient identification data, device status data, medical/treatment data, access authorization data, etc.) stored on the storage system. A variety of processing steps can occur, as will also be appreciated by one having ordinary skill in the art. For example, the storage system can be used by someone with ordinary skill in the art to generate reports and output such reports at step 308, which can be displayed, downloaded and/or printed by the operator. The reports can include a variety of information including information directed to when the patient sought access to the dispensing device and presumably took a dosage of medicaments dispensed therefrom. These reports can be used by medical professionals to determine compliance with the treatment regimen and, thus, make decisions regarding the prescribed treatment, as well as investigate any indicia of addiction, abuse, misuse and the like.

At step 308, alerts can also be outputted (as previously discussed in conjunction with FIG. 2) to the patient, a caretaker, a medical professional and the like. These alerts can be of any type known to one having ordinary skill in the art including, for example, alerts transmitted through phone calls, text messages, emails and audible and/or visual alarms on the dispensing device or via separate communication devices.

Now referring to FIG. 4, which is an exemplary database schema, this figure illustrates the structural aspects of an exemplary database that can be implemented on a server and form a storage system in accordance with at least one exemplary embodiment of the present invention. FIG. 4 has the following relational variables ("relvars"): Algorithm1 402; Algorithms 404; Device_Info 406; Treatment_Info 408; Patient_Info 410; and Patient_Sessions 412. As shown, each relvar has particular attributes where "PK" indicates that the attribute is a primary key and "FK" indicates that the attribute is a foreign key. The other attributes are candidate keys. Note that this database structure is but one of many possible database structures that one with ordinary skill in the art could conceive of for storing data related to the dispensing devices, patients, treatment regimens, device status, inferred information about the times and quantity of medicament dispensing, etc.

Figure 5:
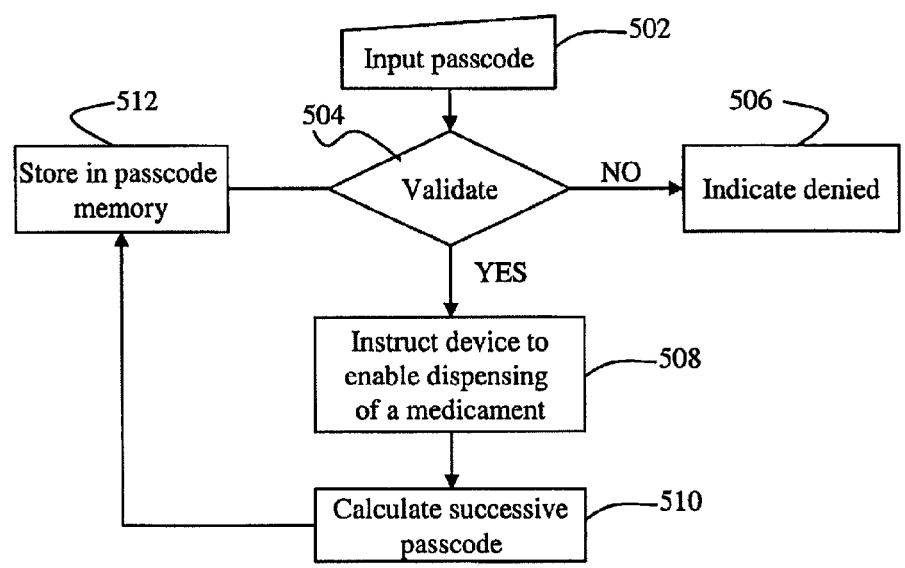
FIG. 5 is a flowchart showing an exemplary process for processing access authorization data by a medicament dispensing device.

Referring to FIG. 5, a process for enabling a medicament dispensing device to dispense a medicament in response to entering access authorization data is shown in accordance with at least one exemplary embodiment of the present invention. The dispensing device can house medicaments and provide access thereto in response to inputting a validated access authorization data. The dispensing device can be constructed so as to be secure when valid access authorization data has not been provided, preventing any sidestepping of the access authorization process. Thus, for example, the dispensing device may be securely sealed and tamper-resistant, and can enable or deny access to the medicaments based on the access authorization data communicated to the drug dispensing device by the user.

Notably, it is not necessary that the dispensing device be connected to a network at any time. In particular, it does not necessarily need to be networked with either the interfacing system or the storage system. The dispensing device can also independently compute and/or store current or subsequent access authorization data periodically and respond to enable or deny access based on current limited-use access authorization data being inputted. Thus, embodiments of the present invention such as IVR embodiments do not depend on a patient having Internet access, which may not be available to a patient for any of a variety of reasons.

Exemplary dispensing devices for use in conjunction with the process shown in FIG. 5 can include memory means such as various types of read only memory ("ROM") for storing instructions and data and processing means such as a central processing unit ("CPU") for processing data. Also, the exemplary dispensing device can include input means such as a keypad, voice recognition system, touch screen, camera, wireless reader, and the like for inputting access authorization data, including all input mechanisms known to one having ordinary skill in the art. Moreover, exemplary dispensing devices can include means such as a display, playable audio files and the like for relaying information to an operator of the dispensing device, including all output systems known to one having ordinary skill in the art. Exemplary dispensing devices can be designed that track the quantity of medicaments contained therein and the times at which the patient seeks access to those medicaments. The device can also implement logic that constrains access to the medicaments to a certain limit of use (e.g., no more than three doses within a 48 hour period). Exemplary devices can also display identifying data such as information reflecting medicament access times, either in an encoded format or in a format readable by a human.

Still referring to FIG. 5, at step 502, a patient (or a person acting on behalf thereof) can input limited-use access authorization data such as a single-use passcode, which may have been obtained from an authorizing system as described herein in conjunction with the process of FIG. 2. Once the access authorization data is inputted at step 502, the dispensing device can validate the access authorization data at step 504. For example, the CPU can compare the access authorization data inputted to a stored passcode and determine if they match. If the inputted access authorization data does not match and, thus, is invalid/denied, then the dispensing device can indicate such via the display (or by like means) at step 506. For example, the dispensing device can display: "No Match"; "Invalid"; "Access Denied"; "Denied"; and the like.

If the inputted access authorization data does match and is therefore validated, the CPU can instruct the dispensing device to enable a dosage of a medicament to be dispensed at step 508. At step 510, subsequent limited-use access authorization data such as the next single-use passcode can be computed based upon an algorithm or any random number generator known to one having ordinary skill in the art.

As one non-limiting example, an algorithm can make use of an initial five or seven digit number that is stored in an access number register such as memory forming part of a control mechanism such as a microcontroller. The first four digits of the five or seven digit number can be used as the initial single-use passcode to enable a medicament dispensing device. After which, the five or seven digit number can be multiplied by a random prime number that can also be stored in the access number register. The last seven or five numbers of the multiplication product can then be stored in the access number register. The first four digits of the multiplication product can be the next single-use passcode. As will be appreciated by one having skill in the art, successive single-use passcodes can thus be calculated ad infinitum. Such exemplary algorithms can produce seemingly random single-use passcodes. Table 1 below is a list of seemingly random single-use passcodes used as the passcodes for at least one exemplary embodiment.

TABLE 1

| Iteration | 5-digit product |
|---|---|
| 1 | 23566 |
| 2 | 44334 |
| 3 | 33222 |
| 4 | 46211 |
| 5 | 22344 |
| 6 | 25446 |
| 7 | 32154 |
| 8 | 25442 |
| 9 | 51224 |
| 10 | 46165 |
| 11 | 32452 |
| 12 | 64352 |
| 13 | 55433 |
| 14 | 16325 |
| 15 | 34314 |
| 16 | 52254 |
| 17 | 24544 |

TABLE 1-continued

| Iteration | 5-digit product |
|---|---|
| 18 | 26152 |
| 19 | 43162 |
| 20 | 42153 |
| 21 | 13266 |
| 22 | 44422 |
| 23 | 26525 |
| 24 | 24151 |
| 25 | 56136 |
| 26 | 34531 |
| 27 | 61534 |
| 28 | 36212 |
| 29 | 36452 |
| 30 | 64562 |
| 31 | 55136 |
| 32 | 32364 |
| 33 | 34313 |
| 34 | 51145 |
| 35 | 13655 |
| 36 | 31561 |
| 37 | 22341 |
| 38 | 31311 |
| 39 | 34661 |
| 40 | 64413 |
| 41 | 63466 |
| 42 | 52464 |
| 43 | 61642 |
| 44 | 36226 |
| 45 | 26561 |
| 46 | 31231 |
| 47 | 42215 |
| 48 | 11634 |
| 49 | 14362 |
| 50 | 25565 |

Still referring to FIG. 5, at step 512, the access authorization data computed at step 510 such as the next single-use passcode can be both stored in the memory of the dispensing device and stored in the storage system accessed by the interfacing server. Alternatively, an algorithm can be used to calculate and determine the next passcode, and the same algorithm should be used by both the interfacing server and the dispensing device to determine the next limited-use access authorization data. Also alternatively, both the device and the interfacing server can have access to separate but identical lists of valid access authorization data.

The limited-use access authorization data can be transmitted to a patient (or person acting on behalf thereof) by the interfacing system in conjunction with a storage system (medical master system). Importantly, the use of the same algorithm or same tables of access authorization data can allow independent calculation and storage of each limited-use access authorization data on both the dispensing device and the exemplary authorizing system of FIG. 2. Thus, it is not necessary that the dispensing device be networked with a storage system because it can have independent processing and storage capabilities for independently determining access authorization data.

In regard to access authorization data generation, particularly single-use passcode generation in accordance with at least one exemplary embodiment, single-use passcodes can be set to change at any desired time, which may occur periodically and/or frequently. As stated above, at the dispensing device level, a microcontroller, as one non-limiting example, can programmatically change the passcode to follow a list of known passcodes, or in accordance with a random number generator such as an algorithm for such a purpose. In general, one with ordinary skill in the art can conceive of a variety of ways to implement a changing series of limited-use access authorization data, and ensure that the same list of limited-use access authorization data can be simultaneously computable at both the drug dispensing device and at the interfacing server.

Alternatively, singularly or in conjunction, the microcontroller can ensure that access authorization data is used for only a certain quantity of medicaments, or access to medicaments over a certain period of time, or a combination of quantity and time frame (e.g., a passcode unlocks the device until a user has dispensed medicaments three time or until twenty-four hours have passed, and thereafter the passcode expires). Also, the microcontroller can track the times at which medicaments are accessed, store that information in memory, and consolidate that information into a status code which encodes information about the access history. It is possible to make this status code visible on a device display screen, for example in response to the pressing of certain keys on the key pad, and this device status data can be communicated as part of identifying data during the interaction between the user and the interfacing server, such that device status data can be communicated to the interfacing server medical master system.

In at least one exemplary embodiment in which the limit of access is single use, the microcontroller can ensure that the access authorization data is used only once and is, thus, truly single-use. For example, the device can invalidate entered access authorization data after one use. Thus, multiple doses could not be dispensed over the designated period of time.

In at least one exemplary embodiment, the interfacing and storage systems can also be configured in parallel to the dispensing device (i.e. reproduce the process used by the dispensing device) so as to be able to provide the current and correct access authorization data, if available, when requested by a user (or person acting on behalf thereof).

In at least one exemplary embodiment, an access authorization data reset mechanism can be provided to address any situations where the dispensing device and authorizing system (i.e. interfacing and storage systems) become out of sync or otherwise need resetting. The reset mechanism may function so as to reset the dispensing device to an initial or otherwise determinable state where the access authorization data may be known or determined.

Also, in exemplary embodiments, two or more sets of access authorization data such as two or more single-use passcodes may be enabled or active during overlapping times. For example, if a first passcode is set to expire shortly after a patient contacts the authorizing system (e.g., a minute), then it may be desirable that the system provide the patient with a second passcode that is not set to expire until a later time (e.g., ten minutes) so that the patient has additional and/or sufficient time to access the needed dosage. As another example, the first passcode could enable access to at most three medicaments over the course of twelve hours, whereas an alternative passcode could enable access to at most four medicaments over the course of twenty-four hours. The interfacing server, in conjunction with the storage system, can follow an algorithm that enables that server to selectively communicate one or none of the valid passcodes, depending on whether it is deemed medically advisable.

Figure 6:
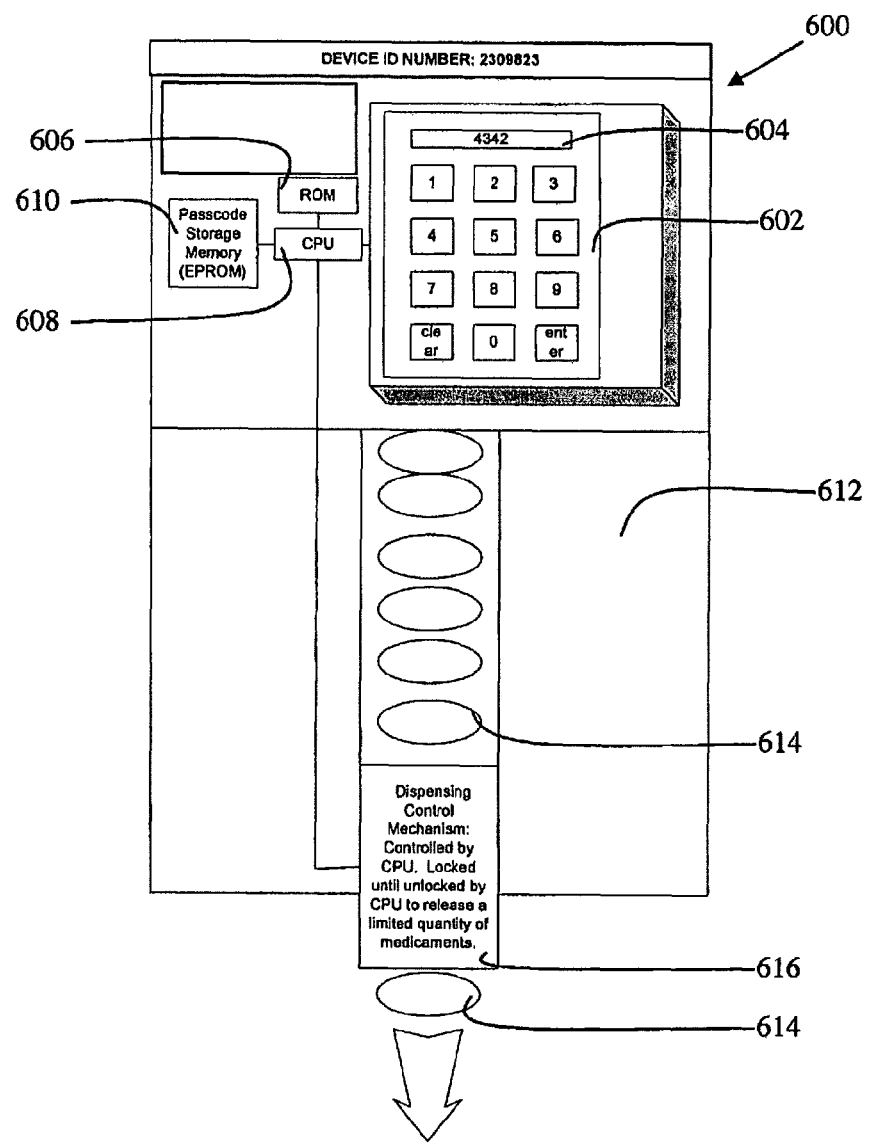
FIG. 6 is a figure showing an exemplary embodiment of a medicament dispensing device.
Figure 7:
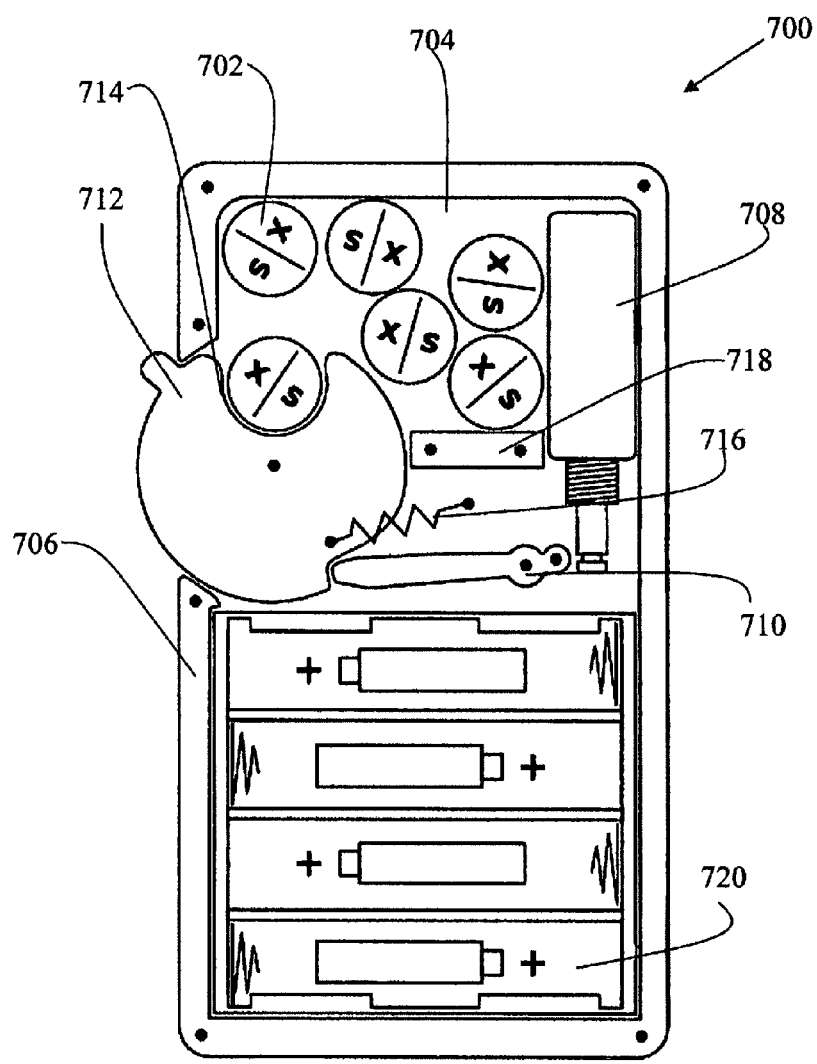
FIG. 7 is a figure showing another exemplary embodiment of a medicament dispensing device in a non-dispensing state.
Figure 8:
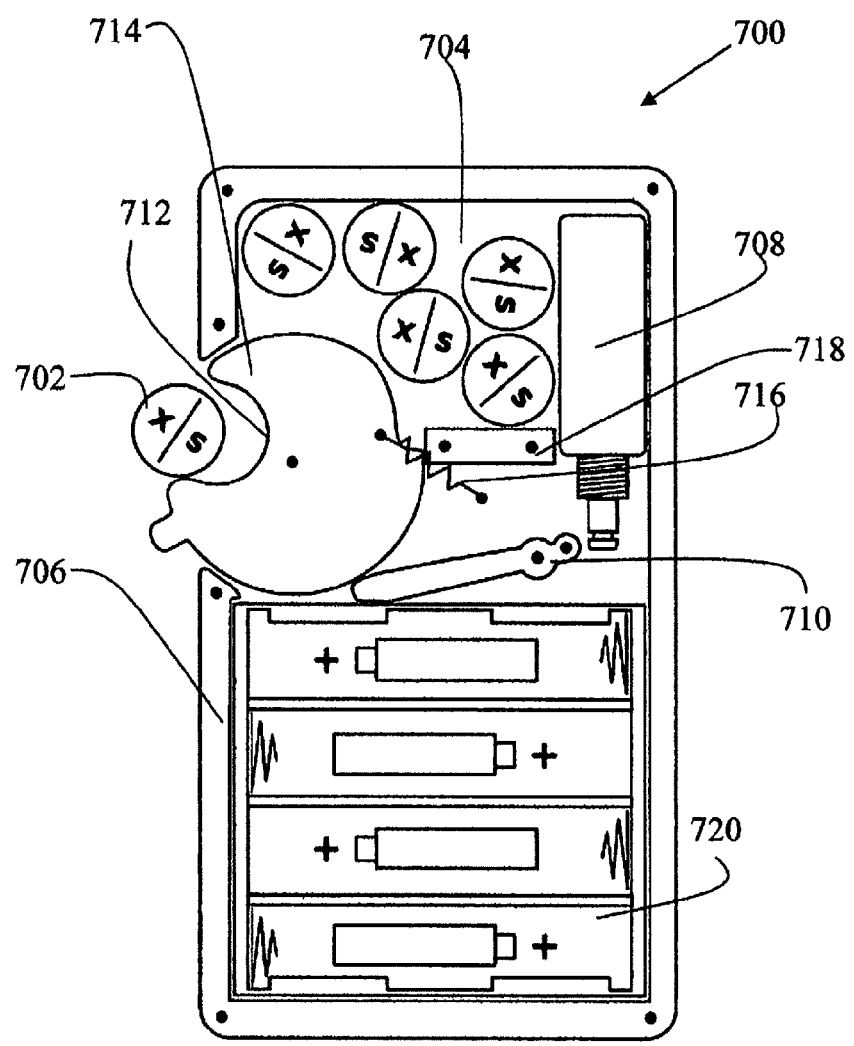
FIG. 8 is a figure showing the medicament dispensing device of FIG. 7 in a dispensing state.

FIGS. 6-8 generally show aspects and configurations for medicament dispensing devices in accordance with at least one exemplary embodiment of the present invention. Exemplary dispensing devices can dispense a dosage of medicaments without providing a patient with insecure access to all medicaments housed in the dispensing device. Dispensing devices can include control mechanisms that enable or disable dispensing activities, or, alternatively singularly or in conjunction, unlock or lock the dispensing devices. A variety of such mechanisms are familiar to one with ordinary skill in the art. Further, exemplary embodiments may be capable of being connected to outside systems and sources, such as those that can be provided through the Internet via wired or wireless connections, although this is not a necessary feature in other exemplary embodiments as previously discussed.

Referring to FIG. 6, exemplary dispensing device 600 includes keypad 602 and display 604. Dispensing device 600 can also include CPU 608 that is operatively connected to main memory 606 such as ROM and passcode storage memory 610. For example, passcode storage memory 610 can be in the form of EPROM. Moreover, dispensing device 600 can include dispensing mechanism 612 for housing medicaments 614 where a medicament 614 can be dispensed by dispensing control mechanism 616 under the direction of CPU 608. In at least one exemplary embodiment, ROM 606 can primarily store instructions and data needed by CPU 608 for the operation of display 604 and dispensing control mechanism 616 as well as for generally validating and computing access authorization data (e.g., the needed algorithm data). Passcode storage memory 610 can primarily be directed to storing passcode data needed by the CPU 608 for validating inputted passcodes and computing subsequent passcodes.

Referring to FIGS. 7 and 8, another exemplary dispensing device is schematically depicted in accordance with at least one exemplary embodiment of the present invention. In FIG. 7, dispensing device 700 is in a locked/disengaged state where medicaments 702 can be securely housed in compartment 706 of housing 704. In at least one exemplary embodiment, the housing 704 of device 700 has a height of about 4.40 inches (vertical length as shown in FIG. 7) and a width of about 2.41 inches (horizontal length as shown in FIG. 7). In other embodiments, housing 704 can have any other suitable dimensions as will be appreciated by one having ordinary skill in the art.

As shown, solenoid 708, which is in a de-energized state, can be operatively associated with lever 710. In turn, lever 710 can be operatively associated with dispensing wheel 712. A holding niche 714 for capturing a dosage of medicaments 702 can be defined in dispensing wheel 712. Spring 716 can be attached to dispensing wheel 712 and be proximate lower boundary 718 of compartment 706.

Electronics package 720 can include control electronics including a processor (e.g., a CPU) and memory means, a power source such as batteries, user interface electronics for providing functionality to a user interface (e.g., a keypad/display) and the like known to one having ordinary skill in the art. The processor of electronics package 720 can be operatively connected to solenoid 708 for energizing solenoid 708.

Upon validation of an access authorization data, a processor can energize solenoid 708 effectuating the engaged state as shown in FIG. 8. The engaged (unlocked) state is effectuated through solenoid 708 (powered by the processor) cooperating with lever 710 that, in turn, cooperates to unlock dispensing wheel 712 such that a patient can manually turn the wheel and dispense a dosage of medicaments 702.

For example, an exemplary code device for enabling a dispensing device to accept input of access authorization data, validate that data and provide a signal output to enable the dispensing device to provide access to medicaments, and thereafter require a new passcode to enable further access to medicaments can include the exemplary code device below:

```
//*****************************************
//  MedicaSafe Prototype Firmware v. 01
//  (c) MedicaSafe, Inc.
//  Contact: zeveland@gmail.com
//  Target uC: ATMEGA168
//
//     a - 6/4/07 - created
//*****************************************
#define MEDICASAFE
// --v-- Includes --v--
#include "global.h"                          //global settings
#include <avr/interrupt.h>                   //interrupt support
#include <avr/eeprom.h>                      //internal EEPROM handling routines (for reading tile ID)
#include "timerx8.h"                         //timer library
#include "medicasafe_helper.h"
// --^-- End Includes --^--
// --v-- Function Prototypes --v--
u08 check_code(void);
// --^-- End Function Prototypes --^--
// --v-- Seven-Segment Messages Defins --v--
#define HELLO_MESSAGE    1
#define OPEN_MESSAGE     2
#define ERROR_MESSAGE    3
#define RESET_MESSAGE    4
// --^-- End Seven-Segment Messages Defines --^--
// --v-- Global Variables --v--
u08 g_next_key;
u32 loop_count = 0;
u08 entered_code[6] = {'b', 'b', 'b', 'b', 'b', 'b'};
// --^-- End Global Variables --^--
int main(void) {
    // --v-- Configure the Ports --v--
    // DDRD, PORTD:
    //    7 - output, low (anode 2)
    //       6 - output, low (anode 4)
    //    5 - output, low (anode 1)
    //    4 - output, low (solenoid)
    //    3 - input, pullup (switch 8)
    //    2 - input, pullup (switch 2)
    //    1 - input, pullup (switch 1)
    //    0 - input, pullup (switch 4)
    //        DDRD: b7-0 - ooooiiii - 11110000 - 0xF0
    //              PORTD: b7-0 - llllpppp - 00001111 - 0x0F
    outb(DDRD, 0xF0);
    outb(PORTD, 0x0F);
    // DDRC, PORTC:
    //    7 - input, pullup (nc)
    //       6 - input, pullup (nc)
    //    5 - input, pullup (switch 7)
    //    4 - input, pullup (switch 5)
    //    3 - input, pullup (switch 6)
    //    2 - input, pullup (switch 3)
    //    1 - output, high (disp oe#)
    //    0 - output, low (disp le)
    //        DDRC: b7-0 - iiiiiioo - 00000011 - 0x03
    //              PORTC: b7-0 - ppppppphl - 11111110 - 0xFE
    outb(DDRC, 0x03);
    outb(PORTC, 0xFE);
    // DDRB, PORTB:
    //    7 - input, no pullup (xtal)
    //       6 - input, no pullup (xtal)
    //    5 - output, low (disp clk)
    //    4 - input, pullup (nc)
    //    3 - output, low (disp sdi)
    //    2 - output, low (anode 6)
    //    1 - output, low (anode 3)
    //    0 - output, low (anode 5)
    //        DDRB: b7-0 - iioioooo - 00101111 - 0x2F
    //              PORTB: b7-0 - nnlpllll - 00010000 - 0x10
    outb(DDRB, 0x2F);
    outb(PORTB, 0x10);
    // --^-- End Port Configuration --^--
    // --v-- Startup Tasks --v--
    timerInit();
    delay_ms(500);
    while (eeprom_is_ready() != 1) {
    }
    delay_ms(500);
    g_next_key = eeprom_read_byte(0x00);
    while ((g_next_key == 0x00) || (g_next_key == 0xFF)) {
```

```
                g_next_key = eeprom_read_byte(0x00);
                u08 i;
                for (i=0; i<255; i++) {
                        display_message(ERROR_MESSAGE);
                }
                turn_off_all_anodes( );
                delay_ms(1000);
        }
        u08 j;
        for (j=0; j<100; j++) {
                display_message(HELLO_MESSAGE);
        }
        // -- -- End Startup Tasks -- --
        // --v-- Program Variables --v--
        u08 current_code_digit = 0;
        u08 prev_sw_state = 0;
        u08 active_key;
        u08 key_down_registered;
        u08 key_down_loop_count;
        #define key_down_thresh 1
        // -- -- End Program Variables -- --
        // --v-- Begin Main Program Loop --v--
        while (1) {
                u08 current_sw_state = return_switch_states( );
                if ((current_sw_state == 0) && (prev_sw_state == 0)) {
                } else if ((prev_sw_state == 0) && (current_sw_state != 0)) {
                        u08 i;
                        for (i=0; i<8; i++) {
                                if (current_sw_state & (0x01 << i)) {
                                        active_key = i+1;
                                }
                        }
                        key_down_registered = 0;
                        key_down_loop_count = loop_count;
                } else if ((prev_sw_state == current_sw_state) &&
(current_sw_state != 0)) {
                        if ((key_down_registered == 0) && (loop_count -
key_down_loop_count > key_down_thresh)) {
                                if (active_key < 7) {
                                        entered_code[current_code_digit] = active_key;
                                        entered_code[current_code_digit + 1] = 'u';
                                        current_code_digit++;
                                } else if ((active_key == 7) && (current_code_digit
== 0)) {
                                        u08 current_code = eeprom_read_byte(0x00);
                                        u08 buf[6] = {'b', 'b', 'b', 'b',
current_code/10, current_code%10};
                                        u08 i;
                                        for (i=0; i<100; i++) {
                                                display_string(buf);
                                        }
                                } else if ((active_key == 7) && (current_code_digit >
0)) {
                                        entered_code[current_code_digit] = 'b';
                                        entered_code[current_code_digit - 1] = 'u';
                                        current_code_digit--;
                                } else if ((active_key == 8) && (entered_code[0] !=
'b')) {
                                        u08 check_code_result = check_code( );
                                        if (check_code_result == 0) {
                                                current_code_digit = 0;
                                        }
                                } else if ((active_key == 8) && (entered_code[0] ==
'b')) {
                                        entered_code[0] = 'u';
                                }
                                key_down_registered = 1;
                        }
                }
                display_string(entered_code);
                prev_sw_state = current_sw_state;
                loop_count++;
                /*
                u08 eeprom_byte = eeprom_read_byte(0x02);
                display_number(1, eeprom_byte);
                delay_ms(1);
                eeprom_byte = eeprom_read_byte(0x03);
                display_number(2, eeprom_byte);
                delay_ms(1);
```

```
                eeprom_byte = eeprom_read_byte(0x04);
                display_number(3, eeprom_byte);
                delay_ms(1);
                eeprom_byte = eeprom_read_byte(0x05);
                display_number(4, eeprom_byte);
                delay_ms(1);
                eeprom_byte = eeprom_read_byte(0x06);
                display_number(5, eeprom_byte);
                delay_ms(1);
                */
        }
        // -- -- End Main Program Loop -- --
}
// --v-- Subroutines --v--
u08 check_code(void) {
        u08 i;
        if ((entered_code[0] == 6) && (entered_code[1] == 6) &&
(entered_code[2] == 6) && (entered_code[3] == 6) && (entered_code[4] == 6) &&
(entered_code[5] == 6)) {
                for (i=0; i<200; i++) {
                        display_message(RESET_MESSAGE);
                }
                eeprom_write_byte(0x00, 1);
                for (i=0; i<6; i++) {
                        entered_code[i] = 'b';
                }
                return 0;
        }
        while (eeprom_is_ready( ) != 1) {
        }
        delay_ms(5);
        u08 current_code = eeprom_read_byte(0x00);
        u08 eeprom_offset = (6 * (current_code-1)) + 2;
        for (i=0; i<5; i++) {
                while (eeprom_is_ready( ) != 1) {
                }
                delay_ms(5);
                u08 eeprom_code_byte = eeprom_read_byte(i + eeprom_offset);
                if (eeprom_code_byte != entered_code[i]) {
                        return 1;
                }
        }
        for (i=0; i<50; i++) {
                display_message(OPEN_MESSAGE);
        }
        turn_off_all_anodes( );
        for (i=0; i<100; i++) {
                activate_solenoid( );
                delay_ms(50);
                deactivate_solenoid( );
                delay_ms(5);
        }
//      for (i=0; i<255; i++) {
//              display_string(eeprom_code_bytes);
//      }
        for (i=0; i<6; i++) {
                entered_code[i] = 'b';
        }
        if (current_code == 50) {
                eeprom_write_byte(0x00, 1);
        } else {
                eeprom_write_byte(0x00, current_code+1);
        }
        return 0;
}
// -- -- End Subroutines -- --
#ifndef MEDICASAFE_HELPER_H_
#define MEDICASAFE_HELPER_H_
#include "global.h"
u08 get_switch_press(void);
u08 return_switch_states(void);
void display_string(u08* string_to_display);
void display_message(u08 message_number);
void show_screen(u08* pdata);
void display_number(u08 seven_seg_number, u08 number_to_display);
void display_character(u08 seven_seg_number, u08 character_unpacked);
void cycle_display_clock(u08 clock_cycles);
void turn_off_all_anodes(void);
void turn_on_anode(u08 anode);
```

```
void turn_off_anode(u08 anode);
void activate_solenoid(void);
void deactivate_solenoid(void);
#endif /*MEDICASAFE_HELPER_H_*/
#include <avr/io.h>                          //IO definitions (port names,
pin names, etc.)
#include <stdlib.h>
#include "global.h"                          //global settings
#include "timerx8.h"
#include "medicasafe_helper.h"
// --v-- Switch Routines --v--
u08 get_switch_press(void) {
        u08 switch_press = 0;
        u08 first_switch_state = return_switch_states( );
        delay_ms(10);
        u08 second_switch_state = return_switch_states( );
        if (first_switch_state == second_switch_state) {
                if (first_switch_state == 0x01)        switch_press = 1;
                if (first_switch_state == 0x02)        switch_press = 2;
                if (first_switch_state == 0x04)        switch_press = 3;
                if (first_switch_state == 0x08)        switch_press = 4;
                if (first_switch_state == 0x10)        switch_press = 5;
                if (first_switch_state == 0x20)        switch_press = 6;
                if (first_switch_state == 0x40)        switch_press = 7;
                if (first_switch_state == 0x80)        switch_press = 8;
        }
        return switch_press;
}
u08 return_switch_states(void) {
        u08 data = 0;
        if (bit_is_clear(SW1_PORT, SW1_PIN))   data |= 0x01;
        if (bit_is_clear(SW2_PORT, SW2_PIN))   data |= 0x02;
        if (bit_is_clear(SW3_PORT, SW3_PIN))   data |= 0x04;
        if (bit_is_clear(SW4_PORT, SW4_PIN))   data |= 0x08;
        if (bit_is_clear(SW5_PORT, SW5_PIN))   data |= 0x10;
        if (bit_is_clear(SW6_PORT, SW6_PIN))   data |= 0x20;
        if (bit_is_clear(SW7_PORT, SW7_PIN))   data |= 0x40;
        if (bit_is_clear(SW8_PORT, SW8_PIN))   data |= 0x80;
        return data;
}
// --^-- End Switch Routines --^--
// --v-- Seven Segment Patterns --v--
// 0x90 is '9' on both - after that:
//    0xFF, 0xFF - blank
//       ??, 0x40 - underscore
u08 number_segments_all_but_last[10] = {0xEE, 0x28, 0xCD, 0x6D, 0x2B, 0x67,
0xE7, 0x2C, 0xEF, 0x6F};
u08 number_segments_last[10] = {0x77, 0x41, 0x3B, 0x6B, 0x4D, 0x6E, 0x7E,
0x43, 0x7F, 0x6F};
#define HELLO_MESSAGE                   1
#define OPEN_MESSAGE                    2
#define ERROR_MESSAGE                   3
#define RESET_MESSAGE                   4
//u08 hello_segments[6] = {0x11, 0x54, 0x34, 0x3D, 0x11};
u08 hello_segments[6] = {0xAB, 0xC7, 0xC2, 0xC2, 0xEE, 0x00};
u08 open_segments[6] = {0xEE, 0x8F, 0xC7, 0xA1, 0x00, 0x00};
u08 error_segments[6] = {0xC7, 0x81, 0x81, 0xE1, 0x81, 0x00};
u08 reset_segments[6] = {0x81, 0xC7, 0x67, 0xC7, 0x29, 0x00};
// --^-- End Seven Segment Patterns --^--
// --v-- High-Level Display Routines --v--
void display_message(u08 message_number) {
        if (message_number == HELLO_MESSAGE) {
                show_screen(hello_segments);
        }
        if (message_number == OPEN_MESSAGE) {
                show_screen(open_segments);
        }
        if (message_number == ERROR_MESSAGE) {
                show_screen(error_segments);
        }
        if (message_number == RESET_MESSAGE) {
                show_screen(reset_segments);
        }
}
void display_string(u08* string_to_display) {
        u08 i;
        u08 unpacked_characters[6];
        for (i=0; i<6; i++) {
                if (string_to_display[i] < 10) {
```

```
                display_number(i, string_to_display[i]);
        } else if (string_to_display[i] == 'u') {
                if (i < 5) {
                        display_character(i, 0x40);
                } else {
                        display_character(i, 0x20);
                }
        } else if (string_to_display[i] == 'b') {
                display_character(i, 0x00);
        }
        delay_ms(1);
    }
}
void show_screen(u08* pdata) {
    u08 i;
    for (i=0; i<6; i++) {
        display_character(i, pdata[i]);
        delay_ms(1);
    }
}
// --^-- End High-Level Display Routines --^--
// --v-- Low-Level Display Routines --v--
void display_number(u08 seven_seg_number, u08 number_to_display) {
    if (seven_seg_number != 5)
        display_character(seven_seg_number,
number_segments_all_but_last[number_to_display]);
    else
        display_character(seven_seg_number,
number_segments_last[number_to_display]);
}
void display_character(u08 seven_seg_number, u08 character_unpacked) {
    u08 i;
    turn_off_all_anodes( );
    DISP_OE_PORT |= _BV(DISP_OE_PIN);       // de-assert OE (active-low):
    DISP_LE_PORT &= ~_BV(DISP_LE_PIN);      // de-assert LE (active-high):
    for (i=0; i<8; i++) {
        if (bit_is_set(character_unpacked, i))
            DISP_SDI_PORT |= _BV(DISP_SDI_PIN);
        else
            DISP_SDI_PORT &= ~_BV(DISP_SDI_PIN);
        cycle_display_clock(1);
    }
    DISP_LE_PORT |= _BV(DISP_LE_PIN);
    delay(10);
    DISP_LE_PORT &= ~_BV(DISP_LE_PIN);
    delay(10);
    DISP_OE_PORT &= ~_BV(DISP_OE_PIN);
    delay(10);
    cycle_display_clock(2);
    turn_on_anode(seven_seg_number);
}
void cycle_display_clock(u08 clock_cycles) {
    u08 i;
    for (i=0; i<clock_cycles; i++) {
        DISP_CLK_PORT |= _BV(DISP_CLK_PIN);
        delay(10);
        DISP_CLK_PORT &= ~_BV(DISP_CLK_PIN);
        delay(10);
    }
}
// --^-- End Low-Level Display Routines --^--
// --v-- Display Anode Control Routines --v--
void turn_off_all_anodes(void) {
    ANODE1_PORT &= ~_BV(ANODE1_PIN);
    ANODE2_PORT &= ~_BV(ANODE2_PIN);
    ANODE3_PORT &= ~_BV(ANODE3_PIN);
    ANODE4_PORT &= ~_BV(ANODE4_PIN);
    ANODE5_PORT &= ~_BV(ANODE5_PIN);
    ANODE6_PORT &= ~_BV(ANODE6_PIN);
}
void turn_on_anode(u08 anode) {
    if (anode == 0)   ANODE1_PORT |= _BV(ANODE1_PIN);
    if (anode == 1)   ANODE4_PORT |= _BV(ANODE4_PIN);
    if (anode == 2)   ANODE2_PORT |= _BV(ANODE2_PIN);
    if (anode == 3)   ANODE5_PORT |= _BV(ANODE5_PIN);
    if (anode == 4)   ANODE3_PORT |= _BV(ANODE3_PIN);
    if (anode == 5)   ANODE6_PORT |= _BV(ANODE6_PIN);
}
void turn_off_anode(u08 anode) {
```

```
        if (anode == 0)   ANODE1_PORT &= ~_BV(ANODE1_PIN);
        if (anode == 1)   ANODE4_PORT &= ~_BV(ANODE4_PIN);
        if (anode == 2)   ANODE2_PORT &= ~_BV(ANODE2_PIN);
        if (anode == 3)   ANODE5_PORT &= ~_BV(ANODE5_PIN);
        if (anode == 4)   ANODE3_PORT &= ~_BV(ANODE3_PIN);
        if (anode == 5)   ANODE6_PORT &= ~_BV(ANODE6_PIN);
}
// ---- End Display Anode Control Routines ----
// --v-- Solenoid Control Routines --v--
void activate_solenoid(void) {
        SOLENOID_PORT |= _BV(SOLENOID_PIN);
}
void deactivate_solenoid(void) {
        SOLENOID_PORT &= ~_BV(SOLENOID_PIN);
}
// ---- End Solenoid Control Routines ----
```

In at least one other exemplary embodiment, an administrator such as a nurse can respond to requests for access authorization data from a patient (or a person acting on behalf thereof). A patient may use a communicative intermediary to contact the administrator. For example, it is contemplated that the administrator can be a nurse employed by a call center for receiving requests for access authorization data. Also, a patient can place a phone call that an administrator can receive, initiate a web-based correspondence with an administrator, transmit a text message viewable by an administrator and the like for requesting access authorization data. A patient can also correspond face-to-face with an administrator if such an option is available.

In such exemplary embodiments, the patient can provide identifying data to the administrator. As will be appreciated by one having ordinary skill in the art, access authorization data can be authorized and/or determined through an administrator operating a computing device or be accomplished manually or a combination of the two. As one non-limiting example, the administrator can operate a computing device capable of authorizing identifying data and providing access authorization data. Alternatively, an administrator can view the medication regimen and a patient's access history and authorize additional access authentication data. As described above, the access authorization data can be used by a patient to access a dosage of medicaments from a dispensing device. Also, the access authorization can be limited-use access authorization data.

The administrator can communicate the access authorization data, if appropriate, to the patient via, for example, a communicative intermediary. Thus, an administrator may communicate the access authorization data over a telephone, through the Internet, via a responsive text message and the like known to one having ordinary skill in the art.

Figure 9:
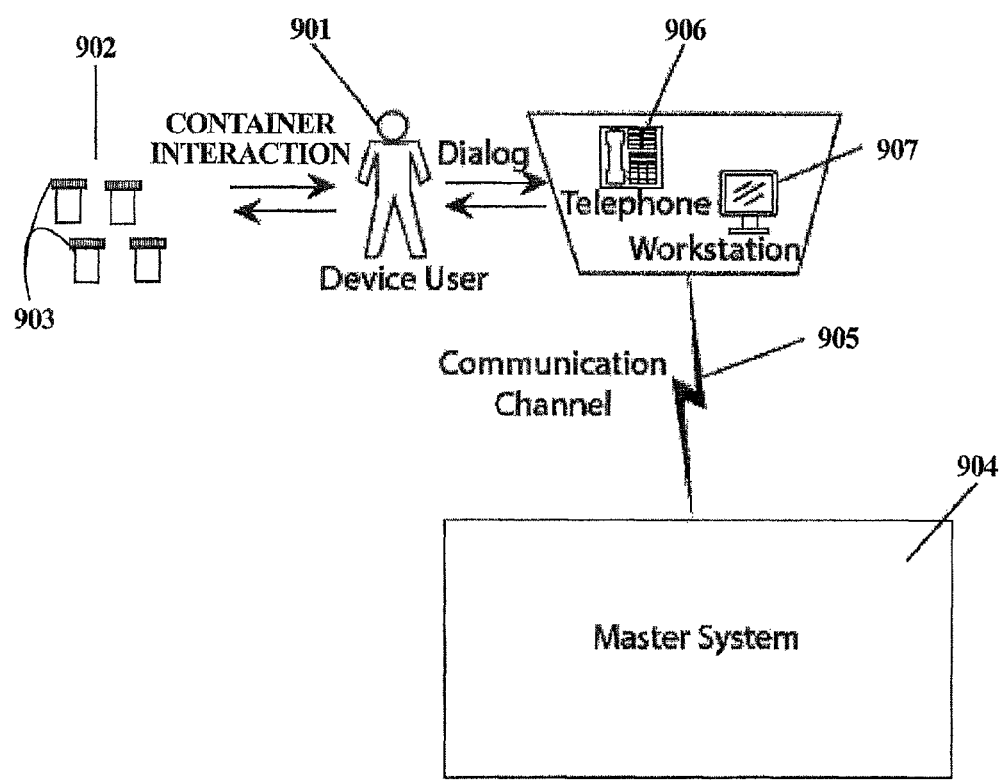
FIG. 9 is an exemplary diagram of the relationship between major components of the invention such as a master data system and a pill container.

FIG. 9 illustrates a high-level overview of another exemplary embodiment of the present invention. A device user 901 is provided medicaments in pill containers 902. Each pill container may be a dispensing device 600, as shown in FIG. 6. Each pill container 902 contains a pill cap 903 that can be locked onto the pill container 902 at the pharmacy and requires some access code, for example a passcode, to unlock the pill cap 903. In order to get the access code to unlock the pill cap 903, the patient 901 contacts master system 904 using communication channel 905. The master system 904 may be similar to system 111 shown in FIG. 1. The communication channel 905 could be, as a non-limiting example, a telephone 906, a network-connected computing device 907, or some other communication device.

The pill cap 903 may electronically log each time the pill cap 903 is removed from the pill bottle. The number of times the pill cap 903 is removed from the pill bottle may be encoded into a status code. The status code may be, as a non-limiting example, a number that is displayed on a pill cap.

The user 901 communicates to master system 904 identifying data, such as the patient's ID or an ID number from the medication container. The master system 904 may generate inquiries to user 901, such, as a non-limiting example, inquiries about the patient's symptoms or about the status code displayed on the medication container. The master system 904 may send to the user 901 access data, such as an access code to unlock a medication container.

Figure 10A:
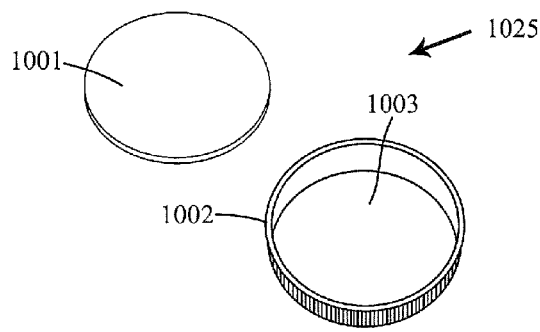
FIGS. 10A through 10F are alternative views of an exemplary diagram illustrating a pill cap and locking mechanism for that cap.
Figure 10B:
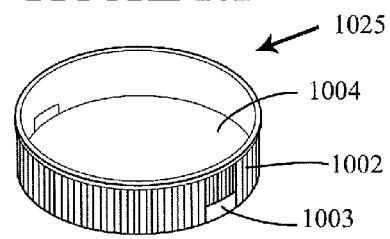
Figure 10C:
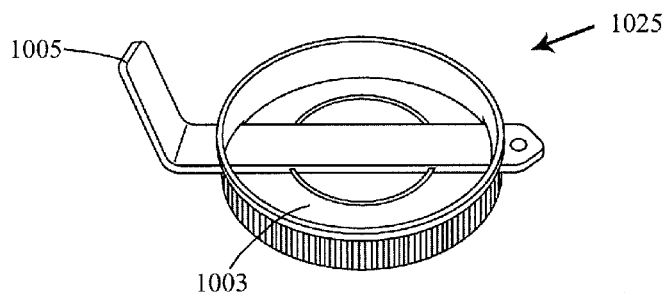
Figure 10D:
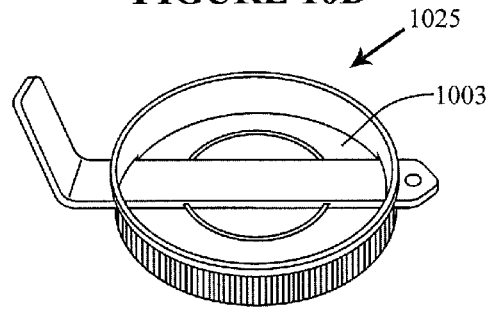
Figure 10E:
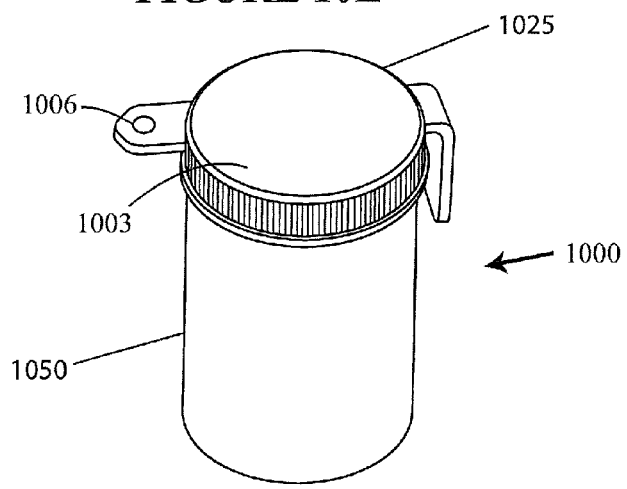
Figure 10F:
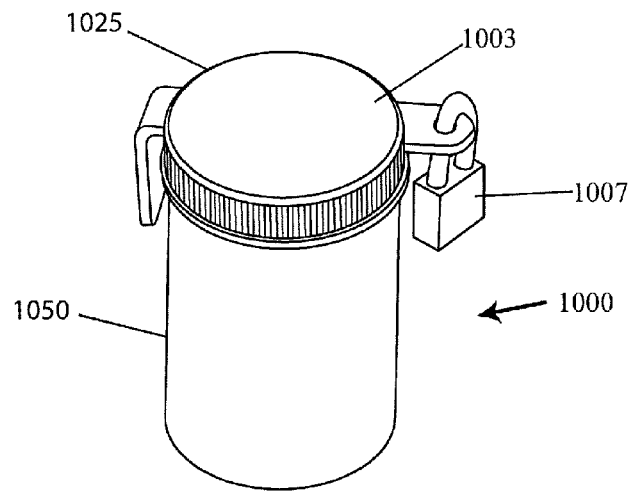
Figure 11:
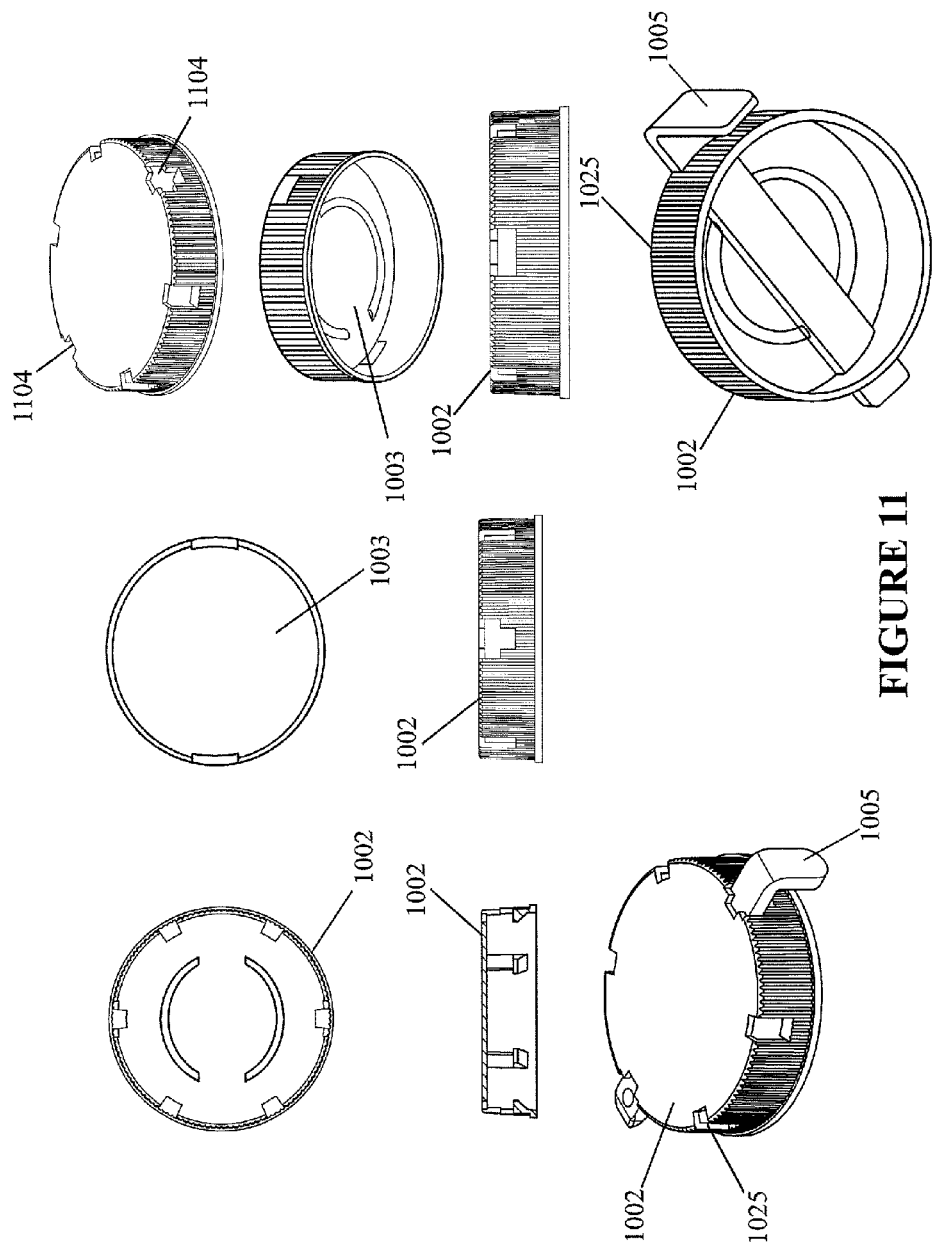
FIG. 11 is an exploded, exemplary diagram of the pill cap of FIG. 11.

A non-limiting exemplary embodiment of pill container 1000 is shown in FIGS. 10A through 11. As shown in FIGS. 10E and 10F, pill container 1000 contains a plastic bottle 1050 and a pill cap 1025. As shown in FIGS. 10A-B, pill cap 1025 is similar to a "push and twist" safety cap. Pill cap 1025 is sized such that it fits onto a standard "safety" pill bottle.

As shown in FIGS. 10A and 10B, the pill cap 1025 contains an inner liner 1001 and an outer shell 1002. The inner liner 1001 fits inside the outer shell 1002. The outer shell 1002 pushes the inner liner 1001 into place on the pill bottle, creating a seal. The outer shell 1002 also contains a ridge 1003. When the cap is on the bottle, the inner liner 1001 serves as a spring for the ridge 1003, keeping the outer shell 1002 sprung up and away from the liner 1001. As shown in FIGS. 10C and 10D, outer shell 1002 contains holes 1004 such that a pin 1005 can slide through the outer shell 1002. Pin 1005 then sits between the inner liner 1001 and the outer shell 1002. FIG. 11 shows exploded details of pill cap 1025, including a more detailed view of outer shell 1002, ridge 1003, holes 1004, and pin 1005. As shown in FIG. 11, the ring shaped ridge 1003 may be abbreviated to create a pathway for the pin 1005.

As shown in FIGS. 10E and 10F, pin 1005 prevents removal of pill cap 1025 from plastic bottle 1050, in that the pin prevents the normal "push down and twist" motion for removing the cap. After the pill cap 1025 is placed on bottle 1050, pin 1005 may then be slid through holes 1004 of pill cap 1025 in order to hold pill cap 1025 and bottle 1050 in place. After pin 1005 is inserted in pill cap 1025, a user can not push the outer shell 1002 down for the normal 'push and twist' motion necessary to remove the cap.

As shown in FIG. 10F, a combination lock 1007 is placed on pin 1005 in order to prohibit a user from accessing the pill container 1000 when combination lock 1007 is in a closed state. The pin 1005 has a hole 1006 through which the shank of a combination lock 1007 can be placed. The combination lock 1007 may be mechanical. Alternatively, the combination lock 1007 may be digital.

Figure 14:
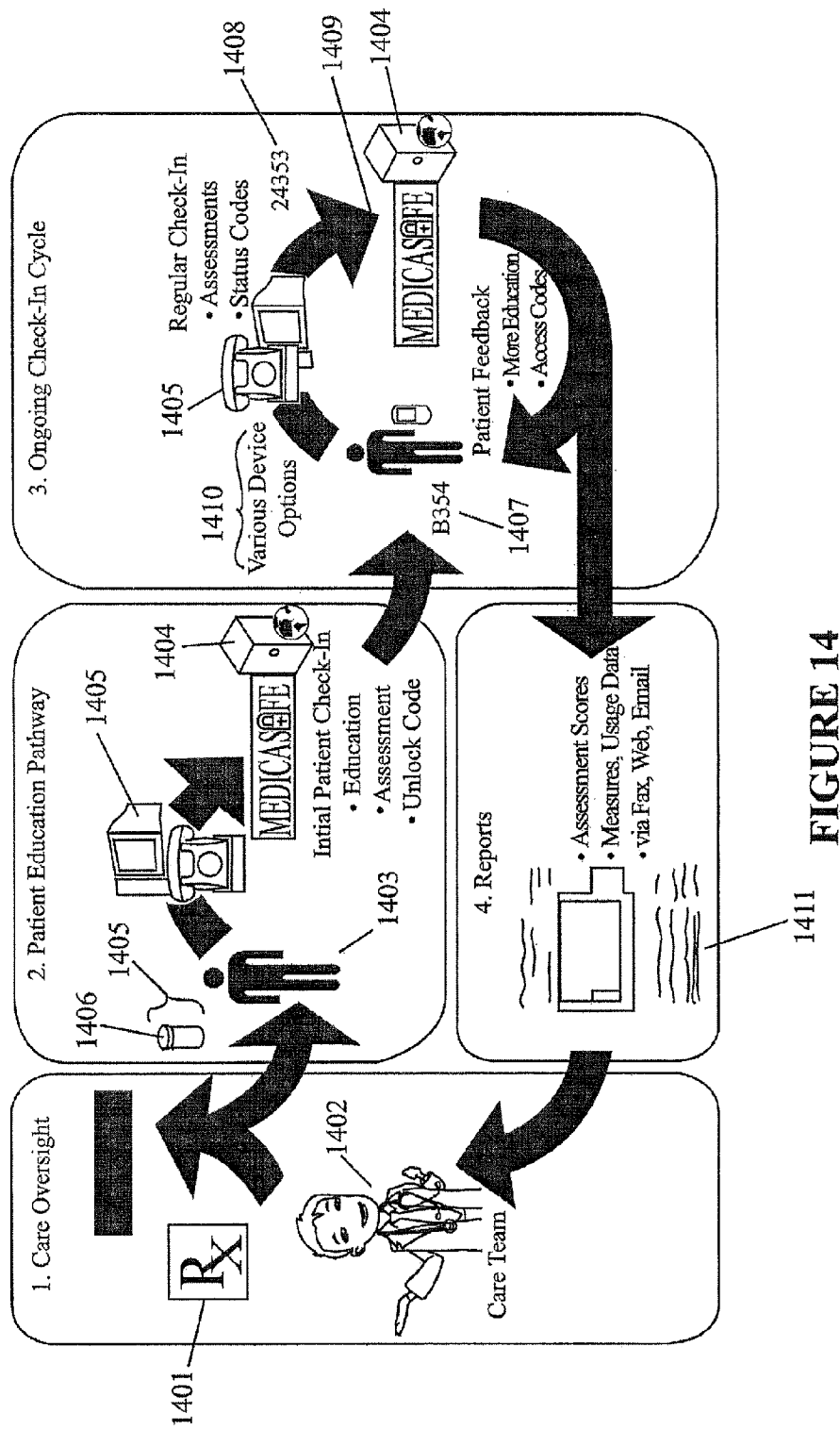
FIG. 14 is an exemplary flow diagram illustrating the check-in process between a user and a master system.

As shown in FIGS. 9 and 14, a user 901 or 1403 may access pill bottle 1000 by contacting a master system 904 or 1404. To open the combination lock, a user contacts master system 904 through a communication channel 905. The user first communicates identifying data to master system 904. Upon verification of the identifying data, the master system 904 communicates an access code to the user. The user inputs the access code into combination lock 1007, which allows the user to unlock combination lock 1007. Upon unlocking combination lock 1007, the user removes the pin 1005 from cap 1025 and accesses the medicaments in bottle 1050.

The medicaments may all be contained in a single pill container 1000. Alternatively, as shown in FIG. 9, the medicaments may be contained in multiple pill containers 903 of the same type as pill container 1000. Each of the pill containers 1000 may store a limited portion or amount of medicaments, where the amount of medicaments represents a drug dosage or a quantity of drugs to be taken over a limited amount of time, e.g. a one-week supply. Each of the pill containers 1000 is locked with a different combination lock of the same type as combination lock 1007. In order to access each of the multiple pill containers, a user would contact master system 904 and, as described above, would obtain an access code. The master system 904 would provide a separate access code for each of the pill containers 903. In order to access a certain pill container, the user may provide identifying data that describes who the user is and which pill container the user is trying to access. For example, a first pill container from the multiple pill containers 903 may correspond with the user's first dosage of certain medicaments. The user would provide the master system 904 with identifying data that indicates the user is trying to access the first pill container. Accordingly, the master system 904 would provide an access code which allows the user to open the combination lock of only the first pill container. The same process would be repeated each time the user wants to access the other pill containers 903.

Another non-limiting exemplary embodiment of a pill container 1200 is shown in FIGS. 12 through 13. The pill container 1200 contains a pill cap 1201 and a processor 1203 that can track and log each opening and removal of the pill cap 1201 from the bottle 1202. The pill cap 1201 contains electronics or any other mechanism that detects the removal of the pill cap 1201 and logs this event. For example, as shown in FIG. 13, a conductive circuit 1301 can be provided or molded into the outer shell of the pill cap 1201, with an open spring 1302 that creates a gap in the circuit 1301 when the pill cap 1201 is off the bottle. The placement of the pill cap 1201 on the bottle 1202 forces spring 1302 to close the gap and complete the circuit 1301. The circuit 1301 is also connected to the processor unit 1203, which can track the opening and closing of the circuit loop when the pill cap 1201 is removed from and placed on the bottle 1202.

The processor 1203 may include a CPU, memory and power. The processor 1203 is able to receive data indicating the pill cap 1201 has been removed and logs this event into a memory by, for example, increasing the count on a counter. The processor 1203 can compress this logged data into a status code that can be displayed to a user and relayed by that user to the master system.

As shown in FIG. 12, the processor 1203 is connected to a display 1204 and a button 1205. When a user presses the button 1205, the CPU displays a number on display 1204 representing the status code to be relayed to the master system. The status code displayed on display 1204 represents an encoded summary of the usage pattern. The status code could be, as a non-limiting example, code "13123" which may indicate that the cap was removed on average once per day in the prior week. Alternatively, the status code could be, as a non-limiting example, code "49232", which may indicate that the cap was removed on average twice per day in the prior week. The number may result from various algorithms for encoding usage patterns.

The pill cap 1201 may be similar to the pill cap 1003 shown in FIGS. 10A through 11. Similar to the pill cap 1003, the pill cap 1201 may contain an inner liner, outer shell, and pin. The pill cap 1201 may also be locked by a combination lock. Alternatively, the pill cap 1201 may have no combination lock.

FIG. 14 is a diagram of an exemplary implementation of the flow process between user 901 and master system 904 shown in FIG. 9. In accordance with an exemplary embodiment of the present invention, a one-month prescription 1401 is provided by a care team 1402, such as a team of healthcare professionals, to a patient 1403. The prescription 1401 is divided by a pharmacy 1404 into four one-week supplies. Each week's supply is placed into a separate pill bottle 1405 with a cap 1406, which may be similar to the pill caps shown in FIG. 10A through FIG. 12. The cap 1406 may be locked with a combination lock 1007 as shown in FIGS. 10A to 10E.

In the exemplary embodiment, the patient 1403 would check-in each week to get an access code 1407 to that week's pill bottle. During the first check-in (via communication channel 905) the patient 1403 undergoes an initial education and assessment program. With the successful completion of the education and assessment program, the patient 1403 is provided with the access code 1407 for one of the pill containers. Patient 1403 will then check-in regularly to access the access code 1407 for each of the four pill containers. During check-in, if the patient 1403 is attempting to check-in too early, for example before one week has passed, or too late, for example after one week has passed, the system may deduce the patient is overdosing or underdosing.

In accordance with an embodiment of the invention, at a point 1409 of the check-in cycle, the patient 1403 may be asked to relay a status code 1408, which is shown on display 1204. If the patient 1403 supplies a valid status code to master system 904, system 904 determines the patient's drug usage is accurate. Note that since the status code 1408 appears to be a random number, the patient will have a hard time forging the status code. During point 1409 of the check-in, the patient 1403 may be asked additional assessment questions. For example, the patient 1403 may be asked to read from ancillary patient devices 1410, which may be glucometers or blood pressure meters. The readings from the devices 1410 can be displayed in either a normal format or in an encoded format.

The master system can use the data collected or inferred at check-in point 1409 to make logical decisions as to whether or not to supply additional access codes 1407 to the patient 1403. The access codes 1407 may enable the patient 1403 to access additional medicaments in the additional bottles 1405. The master system 904 may also decide whether the patient needs to hear additional education messages and the relevant messages will then be relayed to the patient 1403. The master system 904 can also create reports 1411 which can be relayed to the care team 1402. Note that if the patient fails to check-in at expected times, the master system 904 can deduce that the patient is underdosing. This deduction can be used to trigger reminders to the patient 1403 or alerts for the care team 1402.

In further embodiments of the present invention, systems and methods for detecting a likely misuse of a medicament (or generally a controlled substance, such as opioids) is provided. One or more devices which can track removal of a medicament contained therein (or dispensing events) can be used. For example, such devices can include a dispensing device with tracking capabilities such as those described herein, or any dispensing device that tracks and enables reporting on usage patterns. Those devices including 'flow control' mechanisms that prevent the patient from removing multiple doses at once can be particularly useful (as opposed to a standard pill bottle, from which the patient can remove multiple doses when opening the bottle just one time). The dispensing device can include appropriate electronic or digital recording mechanisms to generate a usage pattern of the medicament by the user. The usage pattern can include the time and/or the amount of medicament for each dispensing event. The usage pattern can then be transmitted, e.g., via a communication channel, to a master system (such as a computer system depicted in FIG. 1 and described herein). For example, the usage pattern can be submitted by the user through telephone or internet to an interfacing system that converts the usage pattern into a format usable by the master system. Alternatively, the dispensing device can include appropriate telemetry circuitry to automatically transmit the usage pattern, e.g., as a part of the user identifying data (which may also include other relevant data such as user identification, device identification, the medication being dispensed, etc.), directly or through intermediate relays, via wired connection or wireless connection, to the master system.

To monitor the user's actual consumption of the medication, the user can be prompted to submit to one or more predetermined tests at a pre-scheduled time, at a time based on the time at which a dispensing event occurs (e.g., detected by the dispensing device), or a randomly selected time. If the user complies with the prompt, the test(s) can be performed at the designated time on the user or on a sample extracted from the user, e.g., a urine sample provided by the user. For illustration, the test can be a quantitative urine drug screen that produces outcome measures that are generally known to correlate with the consumption of the medicament (or an active ingredient thereof) during a certain time frame. As an example, there is known a predetermined correlation between the levels of opioids in a person's body during a period 48-72 hours prior to a point at which the urine sample was produced by the person. The test can be either performed at an analytical testing lab, or by using a portable medical monitor, which can be worn or carried by the user. By way of example, the medication may include a drug D, and after the user takes the drug D at time $T_0$, a lab test L is performed at time $T_1$ on user U, producing a test result (e.g., a concentration of drug D in user U's urine sample) denoted as Va. The test result (or lab measure) can be transmitted to the master system via any suitable communication channel, e.g., by a computer at the test site (or the medical monitor) that can automatically transmit the test result to the master system via internet or wireless, mobile and/or other modes of communications commonly known in the art.

Based on the knowledge of the correlation between a user's consumption of a known amount of the medication and a result of a test designed to measure such a consumption, the master system can compute an estimated test result based on the usage pattern received from the user (based on a temporary assumption the user has consumed the medicament according to the usage pattern). Such a computation can take into account certain user characteristics that affect metabolism of the medicament at issue, such as the user's weight, age, activity level, etc. As an illustration, suppose the usage pattern of user U based on the dispensing events recorded and transmitted by a dispensing device used by U may suggest that user U has removed X amount of a drug D from the dispensing device at time $T_0$ (and presumably has taken the drug shortly thereafter). Based on this usage pattern and known metabolism rate and mechanism of the drug D, and taking into account certain relevant characteristics of the user, the master system can compute an estimated or predicted test result (or lab measure), e.g., the concentration of drug D (or a metabolite thereof) in the urine of the user for test L at time $T_1$, as if the user were subjected to test L at time $T_1$. This estimated test result is denoted Ve.

The estimated value Ve can then be compared with the actual test result Va, and the discrepancy between the two values can be used as a basis to determine whether there has been a likely misuse of the drug D by the user. For example, if Ve is greater than Va (or greater than Va plus a predetermined margin), a determination can be made that the user is likely engaged in diversion, that is, it is likely that the user has not actually taken the full amount of drug he or she has removed from the dispensing device. Diversion is particularly common with opioid medications. Conversely, if Va is greater than Ve (or greater than Ve plus a predetermined margin), a determination can be made that the user is likely to have obtained additional drug D (or the active ingredient thereof) from other sources. For example, certain patients have been known to engage in "doctor shopping" where they receive multiple opioid prescriptions from multiple doctors. Some of these patients are also known to supplement prescribed opioids with illicit opioids.

A component of the master system can be used to prompt the user to submit to the test through any communication channels, e.g., via text, email, voice mail, instant message, or the like. The dispensing device can also be configured to provide such a prompt, e.g., by displaying a text message or other visual signals on a digital display of the dispensing device, or by issuing an audio message to the user. The prompt can be given to the user at a randomly selected time after the user has obtained an amount of drug from the dispensing device, and the designated time for the test contained in the prompt can also be randomly selected. For example, the dispensing device can inform the user that he or she must get a lab test on a randomly selected day. As the master system can compute an estimated test result at any arbitrary time based on the known correlation between the consumption of the drug and a likely corresponding lab test result, this random testing procedure can make it more difficult for the user to "beat" the compliance check, thereby enhancing the effectiveness of the identification of diversion or overuse.

While there have been shown and described particular features of the invention as applied to preferred embodiments thereof, it will be understood that various omissions, substitutions, and changes in the form and details of the devices illustrated, and in their operation, may be made by those skilled in the art without departing from the spirit and scope of the invention. For example, a wide variety of containers/devices/caps may be used to enable controlled access to medicaments via a locking mechanism, and to optionally enable the reporting of medicament usage via a status code.

What is claimed is:

1. A method of detecting use of a medicament by a user, comprising:

receiving, by a master system, usage pattern data of a medicament by the user, the usage pattern data generated by a locked dispensing device that is configured to dispense the medicament when unlocked;

receiving, by the master system, a result of at least one predetermined test, which was performed on either the user or a test sample extracted from the user, the test result correlating with an actual consumption of the medicament by the user;

computing, by the master system, an estimated result of a test corresponding to the at least one predetermined test, the estimated result based on the received usage pattern data;

determining whether the user likely misused the medicament by comparing the estimated result and the test result; and if the user is determined to not have likely misused the medicament, providing, from the master system, access authorization data for unlocking the dispensing device for dispensing the medicament.

2. The method of claim 1, wherein the usage pattern data includes one or more dispensing events of a dispensing device containing the medicament.

3. The method of claim 2, wherein the usage pattern data includes information regarding one or both of the time of a dispensing event and the amount of the medicament being dispensed at a dispensing event.

4. The method of claim 1, wherein the dispensing device comprises:
  a processing unit configured to generate the usage pattern data;
  a locking unit, such that the dispensing unit can be locked or unlocked and is capable of dispensing the medicament only when unlocked with the access authorization data; and
  an input evaluation unit configured to receive access authorization data and controlling the locking unit to unlock the dispensing unit in response to receiving the access authorization data.

5. The method of claim 1, wherein computing the estimated result is further based on patient characteristics.

6. The method of claim 1, wherein the usage pattern data is received from the user, and the access authorization data is provided to the user.

7. The method of claim 1, further comprising prompting the user to submit to the at least one predetermined test at a randomly selected time.

8. The method of claim 1, further comprising performing the at least one predetermined test by a portable medical monitor worn by the user.

9. The method of claim 1,
wherein:
  the usage pattern data received by the master system is transmitted from the dispensing device via a communication channel; and
  the access authorization data is transmitted from the master system to the dispensing device via the communication channel.

10. A method of detecting a likely misuse of a medicament by a user, comprising:
  receiving, by a master system, from the user, numerical identifying data that contains a usage pattern data of a medicament by the user, the identifying data generated by a dispensing device that dispenses the medicament;
  receiving, by the master system, a result of at least one predetermined test, which was performed on either the user or a test sample extracted from the user, the test result correlating with an actual consumption of the medicament by the user;
  computing, by the master system, an estimated result of a test corresponding to the at least one predetermined test, the estimated result based on the usage pattern data;
  determining whether the user has likely misused the medicament based on comparing the estimated result and the test result; and
  if the user is determined to not have likely misused the medicament, providing to the user, from the master system, access authorization data for the dispensing device;
wherein:
the dispensing device comprises:
  a processing unit configured to generate identifying data;
  a display unit for displaying the numerical identifying data;
  a locking unit, such that the dispensing unit can be locked or unlocked and is capable of dispensing the medicament only when unlocked with the access authorization data; and
  an input evaluation unit configured to accept an input from the user and controlling the locking unit to unlock the dispensing unit in response to an input of correct access authorization data.

11. A system for detecting use of a medicament by a user, comprising:
  a computer communicatively coupled with a locked dispensing device that dispenses a medicament when unlocked, the computer configured to:
    receive usage pattern data of the medicament by the user, the usage pattern data generated by the dispensing device;
    receive a result of at least one predetermined test, which was performed on either the user or a test sample extracted from the user, the test result correlating with an actual consumption of the medicament by the user;
    based on the usage pattern data, compute an estimated result of a test corresponding to the at least one predetermined test;
    determining whether the user likely misused the medicament by comparing the estimated result and the test result; and
    if the user is determined to not have likely misused the medicament, provide access authorization data for unlocking the dispensing device.

12. The system of claim 11,
wherein the dispensing device comprises:
  a processing unit configured to generate the usage pattern data;
  a locking unit, such that the dispensing unit can be locked or unlocked and is capable of dispensing the medicament only when unlocked with access authorization data;
  an input evaluation unit configured to receive the access authorization data and control the locking unit to unlock the dispensing unit in response to receiving the access authorization data.

13. The system of claim 12, wherein the dispensing device is configured to automatically send the generated usage pattern data to the computer.

14. The system of claim 11, wherein the at least one predetermined test is performed by a portable medical monitor worn by the user.

15. A system for detecting a likely misuse of a medicament by a user, comprising:
  a computer communicatively coupled with a locked dispensing device that contains a medicament, the computer configured to:
    receive usage pattern data of the medicament by the user;

receive a result of at least one predetermined test, which was performed on the user or a test sample extracted from the user, the test result correlating with an actual consumption of the medicament by the user, based on the usage pattern data, compute an estimated result of a test corresponding to the at least one predetermined test;

determine whether the user has likely misused the medicament by comparing the estimated result and the test result; and if the user is determined to not have likely misused the medicament, provide access authorization data for unlocking the dispensing device.

* * * * *